United States Patent
Cantor

(10) Patent No.: US 10,144,966 B2
(45) Date of Patent: *Dec. 4, 2018

(54) METHODS OF NUCLEIC ACID SEQUENCES ANALYSIS USING SOLID SUPPORTS CONTAINING IDENTIFIER SEQUENCES

(71) Applicant: SEQUENOM, INC., San Diego, CA (US)

(72) Inventor: Charles R. Cantor, Del Mar, CA (US)

(73) Assignee: Sequenom, Inc., San Diego, CA (US)

( * ) Notice: Subject to any disclaimer, the term of this patent is extended or adjusted under 35 U.S.C. 154(b) by 164 days.

This patent is subject to a terminal disclaimer.

(21) Appl. No.: 14/687,790

(22) Filed: Apr. 15, 2015

(65) Prior Publication Data

US 2016/0040231 A1    Feb. 11, 2016

Related U.S. Application Data

(63) Continuation of application No. 12/354,749, filed on Jan. 15, 2009, now Pat. No. 9,034,580.

(60) Provisional application No. 61/021,871, filed on Jan. 17, 2008.

(51) Int. Cl.

| C12Q 1/68 | (2018.01) |
| --- | --- |
| C12P 19/34 | (2006.01) |
| C12Q 1/6876 | (2018.01) |
| C12Q 1/6806 | (2018.01) |
| C12Q 1/6837 | (2018.01) |
| C12Q 1/6844 | (2018.01) |

(52) U.S. Cl.
CPC ......... *C12Q 1/6876* (2013.01); *C12Q 1/6806* (2013.01); *C12Q 1/6837* (2013.01); *C12Q 1/6844* (2013.01)

(58) Field of Classification Search
None
See application file for complete search history.

(56) References Cited

U.S. PATENT DOCUMENTS

| 4,469,863 A | 9/1984 | Ts'o et al. |
| --- | --- | --- |
| 5,536,821 A | 7/1996 | Agrawal et al. |
| 5,541,306 A | 7/1996 | Agrawal et al. |
| 5,547,835 A | 8/1996 | Koster |
| 5,614,622 A | 3/1997 | Iyer et al. |
| 5,637,683 A | 6/1997 | Usher et al. |
| 5,637,684 A | 6/1997 | Cook et al. |
| 5,700,922 A | 12/1997 | Cook |
| 5,717,083 A | 2/1998 | Cook et al. |
| 5,719,262 A | 2/1998 | Buchardt et al. |
| 5,739,308 A | 4/1998 | Kandimalla et al. |
| 5,739,314 A | 4/1998 | Roy et al. |
| 5,773,601 A | 6/1998 | Agrawal |
| 5,786,146 A | 7/1998 | Herman et al. |
| 5,886,165 A | 3/1999 | Kandimalla et al. |
| 5,929,226 A | 7/1999 | Padmapriya et al. |
| 5,955,599 A | 9/1999 | Iyer et al. |
| 5,962,674 A | 10/1999 | Iyer et al. |
| 5,977,296 A | 11/1999 | Nielsen et al. |
| 6,043,031 A | 3/2000 | Koster |
| 6,103,463 A | 8/2000 | Chetverin et al. |
| 6,117,992 A | 9/2000 | Iyer |
| 6,133,436 A | 10/2000 | Koster |
| 6,140,482 A | 10/2000 | Iyer |
| 6,274,320 B1 | 8/2001 | Rothberg et al. |
| 6,964,847 B1 * | 11/2005 | Englert ............... C07H 21/04 382/129 |
| 7,169,314 B2 | 1/2007 | Unger |
| 7,244,559 B2 | 7/2007 | Rothberg et al. |
| 7,323,305 B2 | 1/2008 | Leamon et al. |
| 9,034,580 B2 * | 5/2015 | Cantor ............... C12Q 1/6806 435/6.1 |
| 2002/0006617 A1 | 1/2002 | Fan |
| 2003/0082600 A1 | 5/2003 | Olek et al. |
| 2003/0180779 A1 | 9/2003 | Lofton-Day |
| 2004/0110191 A1 | 6/2004 | Winkler et al. |
| 2005/0079510 A1 | 4/2005 | Berka et al. |
| 2005/0112590 A1 | 5/2005 | Van Den Boom et al. |
| 2005/0130173 A1 | 6/2005 | Leamon |
| 2005/0214825 A1 | 9/2005 | Stuelpnagel |
| 2006/0275799 A1 | 12/2006 | Banerjee et al. |

(Continued)

FOREIGN PATENT DOCUMENTS

| EP | 0 269 520 | 6/1988 |
| --- | --- | --- |
| EP | 0 655 501 | 5/1995 |

(Continued)

OTHER PUBLICATIONS

Anker et al., Hum. Mol. Genet. 1:137 (1992).
Banerjee et al., Science 263:227 (1994).
Beckmann et al., (1992) Genomics 12:627-631.
Bentley, "Whole genome resequencing," Curr Opin Genet Dev 16(6):545-552 (2006).
BinLaden et al., PLoS ONE (2007) 2:e197:1-9.
Bird, A., Genes Dev., 16:6-21 (2002).
Blow, "Genomics: the personal side of genomics," Nature. Oct. 4, 2007;449(7162):627-630.
Braslaysky et al., PNAS 100(7): 3960-3964 (2003).
Caruthers, Science 230: 281-286 (1985).

(Continued)

*Primary Examiner* — Young J Kim
(74) *Attorney, Agent, or Firm* — Kilpatrick Townsend & Stockton LLP

(57) ABSTRACT

Improved solid supports and methods for analyzing target nucleotide sequences are provided herein. Certain improvements are directed to efficiently preparing nucleic acids that comprise nucleotide sequences identical to or substantially identical to one or more target nucleotide sequences, or complement thereof. The prepared nucleic acids include a reference sequence that facilitates sequence analysis. The solid supports and methods provided herein minimize the number of steps required by published sequence analysis methodologies, and thereby offer improved sequence analysis efficiency.

17 Claims, 4 Drawing Sheets

(56) References Cited

U.S. PATENT DOCUMENTS

| | | | |
|---|---|---|---|
| 2007/0269817 | A1 | 11/2007 | Shapero et al. |
| 2009/0004665 | A1 | 1/2009 | Brenner |
| 2016/0040231 | A1 | 2/2016 | Cantor |
| 2016/0102352 | A1 | 4/2016 | Cantor |

FOREIGN PATENT DOCUMENTS

| | | |
|---|---|---|
| WO | WO 91/08307 | 6/1991 |
| WO | WO 92/13969 | 8/1992 |
| WO | WO 94/00562 | 1/1994 |
| WO | WO 97/37041 | 10/1997 |
| WO | WO 00/56746 | 9/2000 |
| WO | WO 00/75372 | 12/2000 |
| WO | WO 01/14398 | 3/2001 |
| WO | WO 03/025202 | 3/2003 |
| WO | WO 05/071078 | 8/2005 |
| WO | WO 05/087950 | 9/2005 |
| WO | WO 06/095550 | 9/2006 |

OTHER PUBLICATIONS

Caskey et al., Science 256, 784-789 (1992).
Chakrabarti et al., Nature, 328:543-547 (1987).
Claeboe et al, Nucleic Acids Res. 31(19): 5685-5691 (2003).
Current Protocols in Molecular Biology, John Wiley & Sons, N.Y., 6.3.1-6.3.6 (1989).
Dahl et al., "Multigene amplification and massively parallel sequencing for cancer mutation discovery," PNAS USA May 29, 2007;104(22):9387-9392.
Dear, "One by one: Single Molecule Tools for Genomics", Briefings in Functional Genomic & Proteomics 2003; 1: 397-416.
DNA and Genome Sequencing & Analytical Instrumentation—454 Life Sciences "The Workflow" printed from http://www.454.com/enabling-technology/the-workflow.asp Aug. 16, 2007.
Edwards et al., Nucl. Acids Res. 19:4791 (1991).
German et al., Clin. Genet. 35, 57-69 (1989).
Griffin et al., Pathogenic human viruses in coastal waters. Clinical Microbiol. Rev. 16:129-143, 2003).
Gust et al., Intervirology, 20:1-7 (1983).
Guyader et al., Nature, 328:662-669 (1987).
Hall, Journal of Experimental Biology (2007) 209:1518-1525.
Hames and Higgens, Nucleic Acid Hybridization, A Practical Approach, Ed, IRL Press, 1985.
Harris TD et al., (2008) Science, 320, 106-109.
Hermanson, "Bioconjugate Techniques," Academic Press (1995).
Heym et al., Lancet 344:293-298 (1994).
Jeck et al., "Extending assembly of short DNA sequences to handle error," Bioinformatics 23(21):2942-4 (2007).
Jeffreys et al. (1985) Nature 314:67-73.
Ju et al., "Four-color DNA sequencing by synthesis using cleavable fluorescent nucleotide reversible terminators," Proc Natl Acad Sci USA103(52):19635-40 (2006).
Kojima et al., "PCR amplification from single DNA molecules on magnetic beads in emulsion: application for high-throughput screening of transcription factor targets," Nucleic Acids Research 33(17)e150 1-9 (2005).
Litt et al., (1990) Nucleic Acids Res. 18:4301.
Litt et al., (1990) Nucleic Acids Res. 18:5921.
Luty et al., (1990) Am. J. Hum. Genet. 46:776-783.
Luty et al., (1991) Nucleic Acids Res. 19:4308.
Margulies et al., "Genome sequencing in open microfabricated high density picoliter reactors," Nature: 376-380 (2005).
McKinnon, Hum. Genet. 1 75, 197-208 (1987).
Meyers & Miller, CABIOS 4: 11-17 (1988).
Morris et al., "Molecular mechanisms of multiple drug resistance in clinical isolates of Mycobacterium tuberculosis", J. Infect. Dis. 171:954-960 (1995).
Nakamura et al., (1987) Science 235:1616-1622.
Nakano et al., "Single-molecule PCR using water-in-oil emulsion;" Journal of Biotechnology 102 (2003) 117-124.
Ng et al., "Multiplex sequencing of paired-end ditags (MS-PET): a strategy for the ultra-high-throughput analysis of transcriptomes and genomes.," Nucleic Acids Res. Jul. 13, 2006;34(12):e84 1-10.
Nishimura et al., Nucl. Acids Res. 20:1167 (1992).
Ploos et al., Nucl. Acids Res. 18:4957 (1990).
Polymeropoulos et al., Nucl. Acids Res. 18:7468 (1990).
Polymeropoulos et al., Nucl. Acids Res. 19:195 (1991).
Polymeropoulos et al., Nucl. Acids Res. 19:4018 (1991).
Polymeropoulos et al., Nucl. Acids Res. 19:4306 (1991).
Porreca et al.,"Multiplex amplification of large sets of human exons.," Nat Methods. Nov. 2007;4(11):931-936.
Ratner et al., Nature, 313:227-284 (1985).
Ray et al., "Methods for Evaluating Differential Gene Expression in Tissues and Cells." Drug Development, pp. 50-55 (2005).
Reymer et al., (1995) Nature Genetics 10:28-34.
Rohwer and Edwards, "The phage proteomic tree: a genome based taxonomy for phage", Journal of Bacteriology, 184:4529-4535, (2002).
Schachter et al., "Genetic associations with human longevity at the APOE and ACE loci." (1994) Nature Genetics 6:29-32.
Shendure et al., "Accurate multiplex polony sequencing of an evolved bacterial genome," Science 309(5741):1728-1732 (2005).
Soni and Meller,"Progress toward Ultrafast DNA Sequencing Using Solid-State Nanopores" (2007) Clin Chem 53: 1996-2001.
Tautz, (1989) Nucl. Acids Res. 17:6463-6471.
Venter et al., Science 291:1304-1351 (2001).
Wain Hobson et al., Cell, 40:9-17 (1985).
Wang et al., (1998) Science 280:1077-1082.
Warren et al., "Assembling millions of short DNA sequences using SSAKE," Bioinformatics 23(4):500-1 (2006).
Weber et al., (1989) Am. J. Hum. Genet. 44:388-396.
Weissenbach et al., Nature 359, 794-801 (1992).
Wong, "Chemistry of Protein Conjugation and Cross-Linking," CRC Press (1991).
Yin et al., "Role of hepatitis B virus genotype mixture, subgenotypes C2 and B2 on hepatocellular carcinoma: compared with chronic hepatitis B and asymptomatic carrier state in the same area" Carcinogenesis, 29(9): 1685-1691, (2008).
Zuliani et al., Nucl. Acids Res. 18:4958 (1990).
International Search Report and Written Opinion dated May 20, 2009 for International Application No. PCT/US2009/031169, filed on Jan. 15, 2009.
Extended European Search Report dated Jun. 28, 2013 in European Patent Application No. EP13152418.3, filed Jan. 15, 2009.
Office Action dated Dec. 6, 2010 in U.S. Appl. No. 12/354,749, filed Jan. 15, 2009 and published as US 2009-0202984 on Aug. 13, 2009.
Office Action dated Jul. 21, 2011 in U.S. Appl. No. 12/354,749, filed Jan. 15, 2009 and published as US 2009-0202984 on Aug. 13, 2009.
Office Action dated Jan. 30, 2014 in U.S. Appl. No. 12/354,749, filed Jan. 15, 2009 and published as US 2009-0202984 on Aug. 13, 2009.
Office Action dated Sep. 5, 2014 in U.S. Appl. No. 12/354,749, filed Jan. 15, 2009 and published as US 2009-0202984 on Aug. 13, 2009.
Office Action dated Jan. 16, 2015 in U.S. Appl. No. 12/354,749, filed Jan. 15, 2009 and published as US 2009-0202984 on Aug. 13, 2009.
Office Action dated Aug. 15, 2016 in U.S. Appl. No. 14/973,467, filed Dec. 17, 2015 and published as US 2016-0102352 on Apr. 14, 2016.
Office Action dated Dec. 20, 2016 in U.S. Appl. No. 14/973,467, filed Dec. 17, 2015 and published as US 2016-0102352 on Apr. 14, 2016.
U.S. Appl. No. 14/973,467, Non Final Office Action dated Jun. 27, 2017, 12 pages.
U.S. Appl. No. 14/973,467, "Final Office Action", dated Nov. 27, 2017, 13 pages.
EP 13152418.3, "Office Action", dated Dec. 8, 2016, 4 pages.
U.S. Appl. No. 14/973,467, "Non-Final Office Action", dated Jun. 25, 2018, 16 pages.

(56) References Cited

OTHER PUBLICATIONS

EP 18158658.7, "Extended European Search Report", dated May 4, 2018, 5 pages.

* cited by examiner

METHODS OF NUCLEIC ACID SEQUENCES ANALYSIS USING SOLID SUPPORTS CONTAINING IDENTIFIER SEQUENCES

RELATED APPLICATION

This patent application is a continuation of U.S. patent application Ser. No. 12/354,749, filed on Jan. 15, 2009, now U.S. Pat. No. 9,034,580, entitled "SINGLE MOLECULE NUCLEIC ACID SEQUENCE ANALYSIS PROCESSES AND COMPOSITIONS," naming Charles R. Cantor as applicant, which claims the benefit of U.S. Provisional Patent Application No. 61/021,871, filed on Jan. 17, 2008, entitled SINGLE MOLECULE NUCLEIC ACID SEQUENCE ANALYSIS PROCESSES AND COMPOSITIONS, naming Charles R. Cantor as applicant. The entire content of each of the foregoing patent applications hereby is incorporated by reference herein, including all text, drawings and tables, in jurisdictions providing for such incorporation.

FIELD OF THE INVENTION

The invention pertains generally to the field of nucleic acid sequence analysis and methodology and components for use in such analysis.

SUMMARY

Improved solid supports and methods for analyzing target nucleotide sequences are provided herein. Certain improvements are directed to efficiently preparing nucleic acids that comprise nucleotide sequences identical to or substantially identical to one or more target nucleotide sequences of a sample nucleic acid, or complement thereof. The prepared nucleic acids include reference sequences that facilitate sequence analysis. The solid supports and methods provided herein minimize the number of steps required by published sequence analysis methodologies, and thereby offer improved sequence analysis efficiency.

The invention in part provides a method for preparing sample nucleic acid complements, which comprises: (a) preparing a mixture comprising sample nucleic acid and a solid support under conditions in which a single molecule of the sample nucleic acid hybridizes to a solid support molecule, where: the solid support comprises single-stranded solid phase nucleic acid including a primer sequence, an identifier sequence and a probe sequence; the probe sequence hybridizes to sample nucleic acid when the probe sequence is complementary to a nucleotide sequence in the sample nucleic acid; the solid phase nucleic acid shares a common probe sequence or the solid phase nucleic acid does not share a common probe sequence; and the solid phase nucleic acid shares a common identifier sequence; and the solid support and sample nucleic acid are contacted in the mixture under conditions that allow hybridization of the solid phase nucleic acid to the sample nucleic acid; and (b) contacting the mixture with extension agents under conditions in which the solid phase nucleic acid hybridized to sample nucleic acid is extended; whereby sample nucleic acid complements are prepared. In certain embodiments, the extended solid phase nucleic acids are amplified by an amplification process (e.g., a linear amplification process in which extension agents include a primer that hybridizes to the primer sequence and is extended to generate amplification products).

In embodiments described herein, a solid support may be in a collection of solid supports, and the invention in part provides collections of solid supports and methods in which a collection of solid supports is contacted with sample nucleic acid. In some embodiments pertaining to solid support collections and methods of use, at least one nucleic acid of the solid phase nucleic acid of each of the solid supports in the collection has a unique probe sequence different than a probe sequence of the solid phase nucleic acid of the other solid supports; and the solid phase nucleic acid of each of the solid supports in the collection share a unique identifier sequence different than the identifier sequence of the solid phase nucleic acid of the other solid supports.

The invention also in part provides a method for sequence analysis, which comprises: (a) preparing a mixture comprising sample nucleic acid a solid support under conditions in which a single molecule of the sample nucleic acid hybridizes to a solid support molecule, where: the solid support comprises single-stranded solid phase nucleic acid comprising a primer sequence, an identifier sequence and a probe sequence; the probe sequence hybridizes to sample nucleic acid when the probe sequence is complementary to a nucleotide sequence in the sample nucleic acid; the solid phase nucleic acid shares a common probe sequence or the solid phase nucleic acid does not share a common probe sequence; and the solid phase nucleic acid shares a common identifier sequence; and the sample nucleic acid and the solid support are contacted in the mixture under conditions that allow hybridization of the solid phase nucleic acid to the sample nucleic acid; (b) contacting the mixture with extension agents under conditions in which solid phase nucleic acid hybridized to the sample nucleic acid is extended; (c) amplifying the extended solid phase nucleic acid of (b); and (d) analyzing the sequences of the amplification products of (c); whereby the target nucleic acid sequence is analyzed.

Also, the invention in part provides a method for obtaining sequence information of a target nucleic acid, which comprises: (a) preparing a mixture comprising sample nucleic acid and a solid support under conditions in which a single molecule of the sample nucleic acid hybridizes to a solid support molecule, where: the solid support comprises single-stranded solid phase nucleic acid having a primer sequence, an identifier sequence and a probe sequence; the probe sequence hybridizes to sample nucleic acid when the probe sequence is complementary to a nucleotide sequence in the sample nucleic acid; the solid phase nucleic acid shares a common probe sequence or the solid phase nucleic acid does not share a common probe sequence; the solid phase nucleic acid shares a common identifier sequence; and the sample nucleic acid is nucleic acid from an organism that has been subject to fragmentation and/or specific cleavage; and the sample nucleic acid and the solid support are contacted in the mixture under conditions that allow hybridization of the solid phase nucleic acid to the sample nucleic acid; (b) contacting the mixture with extension agents under conditions in which solid phase nucleic acid hybridized to sample nucleic acid is extended; (c) amplifying the extended solid phase nucleic acid of (b); (d) determining the nucleotide sequences of the amplification products of (c); and (e) constructing sequence information of the target nucleic acid from the nucleotide sequences of (d).

The invention also in part provides a solid support comprising single-stranded solid phase nucleic acid having an identifier sequence and a probe sequence, where: the probe sequence hybridizes to sample nucleic acid when the probe sequence is complementary to a nucleotide sequence in the sample nucleic acid; the solid phase nucleic acid shares a common probe sequence or the solid phase nucleic acid does not share a common probe sequence; and the solid phase nucleic acid shares a common identifier sequence. Such a solid support can be in a collection of solid supports as described herein.

The invention also in part provides a method for manufacturing a solid support having single-stranded solid phase nucleic acid, which comprises: (a) sequentially linking nucleotides to a nucleotide covalently linked to the solid support whereby each of the solid phase nucleic acid is prepared and in association with the solid support; or (b) linking each single-stranded nucleic acid in solution phase to the solid support whereby the single-stranded solid phase nucleic acid is in association with the solid support; where: the single-stranded solid phase nucleic acid comprise an identifier sequence and a probe sequence; the probe sequence is complementary to a target nucleotide sequence; the nucleic acid shares a common probe sequence or the nucleic acid does not share a common probe sequence; and the nucleic acid shares a common identifier sequence.

In certain embodiments, the solid support is in a collection of solid supports; at least one nucleic acid of the solid phase nucleic acid of each of the solid supports in the collection has a unique probe sequence different than a probe sequence of the solid phase nucleic acid of the other solid supports; and the solid phase nucleic acid of each of the solid supports in the collection share a unique identifier sequence different than the identifier sequence of the solid phase nucleic acid of the other solid supports.

Also, the invention in part provides a substrate comprising a collection of beads oriented in an array, where: each bead is in association with single-stranded nucleic acid; the solid phase nucleic acid comprises an identifier sequence and a probe sequence; the probe sequence hybridizes to sample nucleic acid when the probe sequence is complementary to a nucleotide sequence in the sample nucleic acid; at least one nucleic acid of the solid phase nucleic acid of each of the solid supports in the collection has a unique probe sequence different than a probe sequence of the solid phase nucleic acid of the other solid supports; and the solid phase nucleic acid of each of the solid supports in the collection share a unique identifier sequence different than the identifier sequence of solid phase nucleic acid of the other solid supports.

The invention also in part provides a kit comprising a solid support having single-stranded solid phase nucleic acid, one or more agents that can extend solid phase nucleic acid hybridized to sample nucleic acid; and instructions for using the solid support and the one or more reagents; where: the solid phase nucleic acid comprises an identifier sequence and a probe sequence; the probe sequence hybridizes to sample nucleic acid when the probe sequence is complementary to a nucleotide sequence in the sample nucleic acid; the solid phase nucleic acid shares a common probe sequence or the solid phase nucleic acid does not share a common probe sequence; and the solid phase nucleic acid shares a common identifier sequence. In some embodiments, the solid support is in a collection of solid supports; at least one nucleic acid of the solid phase nucleic acid of each of the solid supports in the collection has a unique probe sequence different than a probe sequence of the solid phase nucleic acid of the other solid supports; and the solid phase nucleic acid of each of the solid supports in the collection share a unique identifier sequence different than the identifier sequence of solid phase nucleic acid of the other solid supports.

Certain embodiments and features of the invention are described in greater detail in the following description, claims and drawings.

BRIEF DESCRIPTION OF THE DRAWINGS

The drawings illustrate features of certain embodiments of the invention.

DETAILED DESCRIPTION

Figure 1A:
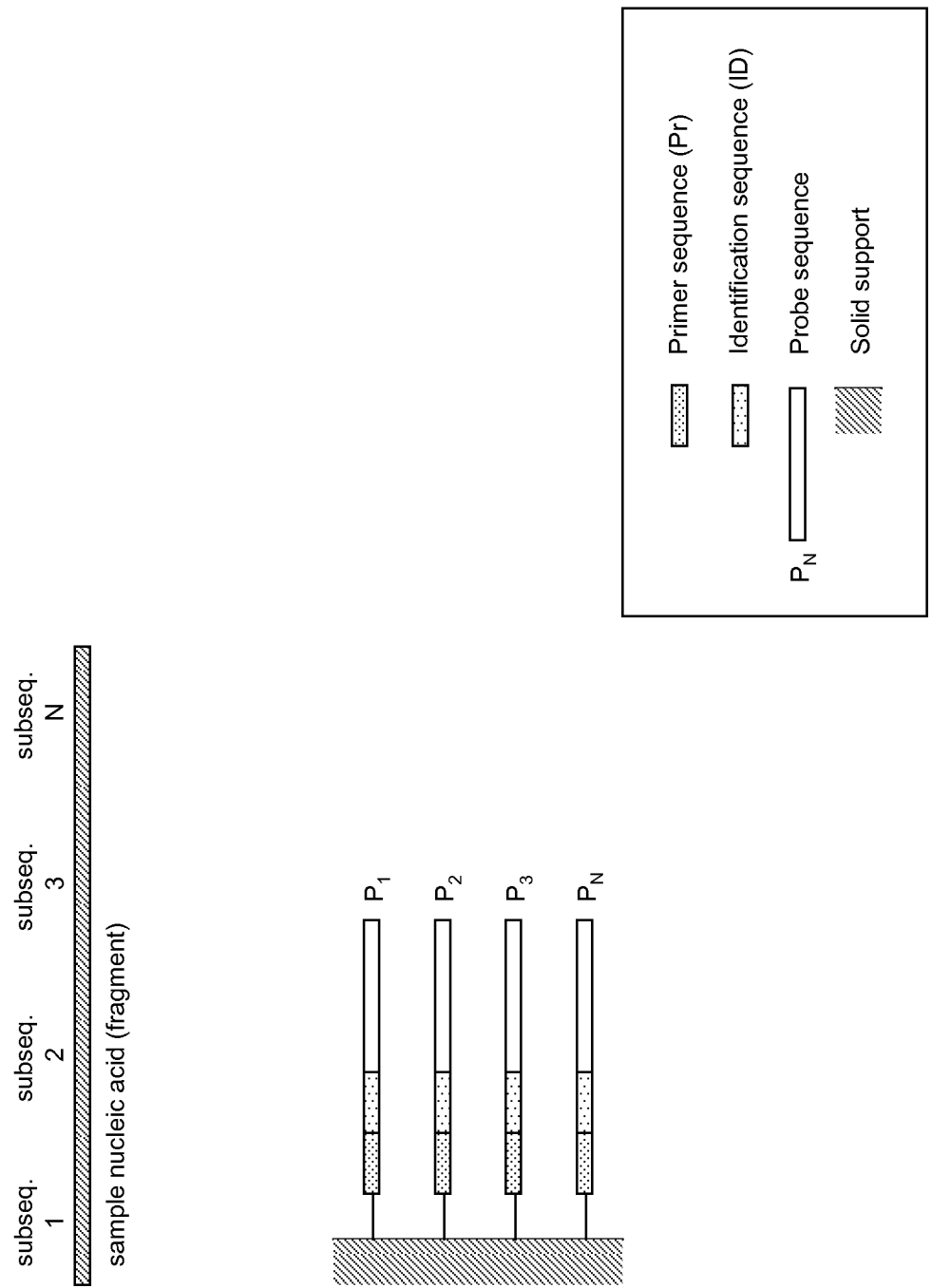
FIGS. 1A-1C shows examples of solid support embodiments.

Improved nucleic acid sequence analysis processes and solid supports described herein find multiple uses in research and clinical applications. Such processes and solid supports can be utilized, for example, to: (a) rapidly determine whether a particular target sequence is present in a sample; (b) perform mixture analysis, e.g., identify a mixture and/or its composition or determine the frequency of a target sequence in a mixture (e.g., mixed communities, quasispecies); (c) detect sequence variations (e.g., mutations, single nucleotide polymorphisms) in a sample; (d) perform haplotyping determinations; (e) perform microorganism (e.g., pathogen) typing; (f) detect the presence or absence of a microorganism target sequence in a sample; (g) identify disease markers; (h) detect microsatellites; (i) identify short tandem repeats; (j) identify an organism or organisms; (k) detect allelic variations; (l) determine allelic frequency; (m) determine methylation patterns; (n) perform epigenetic determinations; (o) re-sequence a region of a biomolecule; (p) human clinical research and medicine (e.g. cancer marker detection, sequence variation detection; detection of sequence signatures favorable or unfavorable for a particular drug administration), (q) HLA typing; (r) forensics; (s) vaccine quality control; (t) treatment monitoring; (u) vector identity; (v) perform vaccine or production strain quality control, (w) detect test strain identity, (x) identify a specific viral nucleic acid sequence or sequences in a viral mixture or population (e.g., hepatitis mixtures, HIV mixtures, mixed viral populations as might be found in an immuno-deficient, or immuno-compromised organism). Certain aspects of the invention are described hereafter.

Sample Nucleic Acid

Sample nucleic acid may be derived from one or more samples or sources. As used herein, "nucleic acid" refers to polynucleotides such as deoxyribonucleic acid (DNA) and ribonucleic acid (RNA). The term should also be understood to include, as equivalents, derivatives, variants and analogs of RNA or DNA made from nucleotide analogs, single (sense or antisense) and double-stranded polynucleotides. It is understood that the term "nucleic acid" does not refer to or infer a specific length of the polynucleotide chain, thus nucleotides, polynucleotides, and oligonucleotides are also included in the definition. Deoxyribonucleotides include deoxyadenosine, deoxycytidine, deoxyguanosine and deoxythymidine. For RNA, the uracil base is uridine. A source or sample containing sample nucleic acid(s) may contain one or a plurality of sample nucleic acids. A plurality of sample nucleic acids as described herein refers to at least 2 sample nucleic acids and includes nucleic acid sequences that may be identical or different. That is, the sample nucleic acids may all be representative of the same nucleic acid sequence, or may be representative of two or more different nucleic acid sequences (e.g., from 1, 2, 3, 4, 5, 6, 7, 8, 9, 10, 11, 12, 13, 14, 15, 16, 17, 18, 19, 20, 50, 100, 1000 or more sequences).

A sample may be collected from an organism, mineral or geological site (e.g., soil, rock, mineral deposit, combat theater), forensic site (e.g., crime scene, contraband or suspected contraband), or a paleontological or archeological site (e.g., fossil, or bone) for example. A sample may be a "biological sample," which refers to any material obtained from a living source or formerly-living source, for example, an animal such as a human or other mammal, a plant, a bacterium, a fungus, a protist or a virus. The biological sample can be in any form, including without limitation a solid material such as a tissue, cells, a cell pellet, a cell extract, or a biopsy, or a biological fluid such as urine, blood, saliva, amniotic fluid, exudate from a region of infection or inflammation, or a mouth wash containing buccal cells, urine, cerebral spinal fluid and synovial fluid and organs. A sample also may be isolated at a different time point as compared to another sample, where each of the samples are from the same or a different source. A sample nucleic acid may be from a nucleic acid library, such as a cDNA or RNA library, for example. A sample nucleic acid may be a result of nucleic acid purification or isolation and/or amplification of nucleic acid molecules from the sample. Sample nucleic acid provided for sequence analysis processes described herein may contain nucleic acid from one sample or from two or more samples (e.g., from 1, 2, 3, 4, 5, 6, 7, 8, 9, 10, 11, 12, 13, 14, 15, 16, 17, 18, 19 or 20 samples). A sample nucleic acid sample can contain host and non-host sample nucleic acid, and in some embodiments, a sample may contain two or more different species of sample nucleic acid (e.g., mutant vs. wild-type, transplants, forensics, mother vs. fetus).

Sample nucleic acid may comprise or consist essentially of any type of nucleic acid suitable for use with processes of the invention, such as sample nucleic acid that can hybridize to solid phase nucleic acid (described hereafter), for example. A sample nucleic in certain embodiments can comprise or consist essentially of DNA (e.g., complementary DNA (cDNA), genomic DNA (gDNA) and the like), RNA (e.g., message RNA (mRNA), short inhibitory RNA (siRNA), ribosomal RNA (rRNA), tRNA and the like), and/or DNA or RNA analogs (e.g., containing base analogs, sugar analogs and/or a non-native backbone and the like). A nucleic acid can be in any form useful for conducting processes herein (e.g., linear, circular, supercoiled, single-stranded, double-stranded and the like). A nucleic acid may be, or may be from, a plasmid, phage, autonomously replicating sequence (ARS), centromere, artificial chromosome, chromosome, a cell, a cell nucleus or cytoplasm of a cell in certain embodiments. A sample nucleic acid in some embodiments is from a single chromosome (e.g., a nucleic acid sample may be from one chromosome of a sample obtained from a diploid organism).

Sample nucleic acid may be provided for conducting methods described herein without processing of the sample(s) containing the nucleic acid in certain embodiments. In some embodiments, sample nucleic acid is provided for conducting methods described herein after processing of the sample(s) containing the nucleic acid. For example, a sample nucleic acid may be extracted, isolated, purified or amplified from the sample(s). The term "isolated" as used herein refers to nucleic acid removed from its original environment (e.g., the natural environment if it is naturally occurring, or a host cell if expressed exogenously), and thus is altered "by the hand of man" from its original environment. An isolated nucleic acid generally is provided with fewer non-nucleic acid components (e.g., protein, lipid) than the amount of components present in a source sample. A composition comprising isolated sample nucleic acid can be substantially isolated (e.g., about 90%, 91%, 92%, 93%, 94%, 95%, 96%, 97%, 98%, 99% or greater than 99% free of non-nucleic acid components). The term "purified" as used herein refers to sample nucleic acid provided that contains fewer nucleic acid species than in the sample source from which the sample nucleic acid is derived. A composition comprising sample nucleic acid may be substantially purified (e.g., about 90%, 91%, 92%, 93%, 94%, 95%, 96%, 97%, 98%, 99% or greater than 99% free of other nucleic acid species). The term "amplified" as used herein refers to subjecting nucleic acid of a sample to a process that linearly or exponentially generates amplicon nucleic acids having the same or substantially the same nucleotide sequence as the nucleotide sequence of the nucleic acid in the sample, or portion thereof.

Sample nucleic acid also may be processed by subjecting nucleic acid to a method that generates nucleic acid fragments, in certain embodiments, before providing sample nucleic acid for a process described herein. In some embodiments, sample nucleic acid subjected to fragmentation or cleavage may have a nominal, average or mean length of about 5 to about 10,000 base pairs, about 100 to about 1,000 base pairs, about 100 to about 500 base pairs, or about 10, 15, 20, 25, 30, 35, 40, 45, 50, 55, 60, 65, 70, 75, 80, 85, 90, 95, 100, 200, 300, 400, 500, 600, 700, 800, 900, 1000, 2000, 3000, 4000, 5000, 6000, 7000, 8000, 9000 or 10000 base pairs. Fragments can be generated by any suitable method known in the art, and the average, mean or nominal length of nucleic acid fragments can be controlled by selecting an appropriate fragment-generating procedure. In certain embodiments, sample nucleic acid of a relatively shorter length can be utilized to analyze sequences that contain little sequence variation and/or contain relatively large amounts of known nucleotide sequence information. In some embodiments, sample nucleic acid of a relatively longer length can be utilized to analyze sequences that contain greater sequence variation and/or contain relatively small amounts of unknown nucleotide sequence information.

Sample nucleic acid fragments often contain overlapping nucleotide sequences, and such overlapping sequences can facilitate construction of a nucleotide sequence of the previously non-fragmented sample nucleic acid, or a portion thereof. For example, one fragment may have subsequences x and y and another fragment may have subsequences y and z, where x, y and z are nucleotide sequences that can be 5 nucleotides in length or greater. Overlap sequence y can be utilized to facilitate construction of the x-y-z nucleotide sequence in nucleic acid from a sample. Sample nucleic acid may be partially fragmented (e.g., from an incomplete or terminated specific cleavage reaction) or fully fragmented in certain embodiments.

Sample nucleic acid can be fragmented by various methods, which include, without limitation, physical, chemical and enzymic processes. Examples of such processes are described in U.S. Patent Application Publication No. 20050112590 (published on May 26, 2005, entitled "Fragmentation-based methods and systems for sequence variation detection and discovery," naming Van Den Boom et al.). Certain processes can be selected to generate non-specifically cleaved fragments or specifically cleaved fragments. Examples of processes that can generate non-specifically cleaved fragment sample nucleic acid include, without limitation, contacting sample nucleic acid with apparatus that expose nucleic acid to shearing force (e.g., passing nucleic acid through a syringe needle; use of a French press); exposing sample nucleic acid to irradiation (e.g., gamma, x-ray, UV irradiation; fragment sizes can be controlled by irradiation intensity); boiling nucleic acid in water (e.g., yields about 500 base pair fragments) and exposing nucleic acid to an acid and base hydrolysis process.

Sample nucleic acid may be specifically cleaved by contacting the nucleic acid with one or more specific cleavage agents. The term "specific cleavage agent" as used herein refers to an agent, sometimes a chemical or an enzyme, that can cleave a nucleic acid at one or more specific sites. Specific cleavage agents often will cleave specifically according to a particular nucleotide sequence at a particular site.

Examples of enzymic specific cleavage agents include without limitation endonucleases (e.g., DNase (e.g., DNase I, II); RNase (e.g., RNase E, F, H, P); Cleavase™ enzyme; Taq DNA polymerase; E. coli DNA polymerase I and eukaryotic structure-specific endonucleases; murine FEN-1 endonucleases; type I, II or III restriction endonucleases such as Acc I, Afl III, Alu I, Alw44 I, Apa I, Asn I, Ava I, Ava II, BamH I, Ban II, Bcl I, Bgl I. Bgl II, Bln I, Bsm I, BssH II, BstE II, Cfo I, Cla I, Dde I, Dpn I, Dra I, EcIX I, EcoR I, EcoR I, EcoR II, EcoR V, Hae II, Hae II, Hind II, Hind III, Hpa I, Hpa II, Kpn I, Ksp I, Mlu I, MIuN I, Msp I, Nci I, Nco I, Nde I, Nde II, Nhe I, Not I, Nru I, Nsi I, Pst I, Pvu I, Pvu II, Rsa I, Sac I, Sal I, Sau3A I, Sca I, ScrF I, Sfi I, Sma I, Spe I, Sph I, Ssp I, Stu I, Sty I, Swa I, Taq I, Xba I, Xho I); glycosylases (e.g., uracil-DNA glycolsylase (UDG), 3-methyladenine DNA glycosylase, 3-methyladenine DNA glycosylase II, pyrimidine hydrate-DNA glycosylase, FaPy-DNA glycosylase, thymine mismatch-DNA glycosylase, hypoxanthine-DNA glycosylase, 5-Hydroxymethyluracil DNA glycosylase (HmUDG), 5-Hydroxymethylcytosine DNA glycosylase, or 1,N6-etheno-adenine DNA glycosylase); exonucleases (e.g., exonuclease III); ribozymes, and DNAzymes. Sample nucleic acid may be treated with a chemical agent, or synthesized using modified nucleotides, and the modified nucleic acid may be cleaved. In non-limiting examples, sample nucleic acid may be treated with (i) alkylating agents such as methylnitrosourea that generate several alkylated bases, including N3-methyladenine and N3-methylguanine, which are recognized and cleaved by alkyl purine DNA-glycosylase; (ii) sodium bisulfite, which causes deamination of cytosine residues in DNA to form uracil residues that can be cleaved by uracil N-glycosylase; and (iii) a chemical agent that converts guanine to its oxidized form, 8-hydroxyguanine, which can be cleaved by formamidopyrimidine DNA N-glycosylase. Examples of chemical cleavage processes include without limitation alkylation, (e.g., alkylation of phosphorothioate-modified nucleic acid); cleavage of acid lability of P3'-N5'-phosphoroamidate-containing nucleic acid; and osmium tetroxide and piperidine treatment of nucleic acid.

As used herein, the term "complementary cleavage reactions" refers to cleavage reactions that are carried out on the same sample nucleic acid using different cleavage reagents or by altering the cleavage specificity of the same cleavage reagent such that alternate cleavage patterns of the same target or reference nucleic acid or protein are generated. In certain embodiments, sample nucleic acid may be treated with one or more specific cleavage agents (e.g., 1, 2, 3, 4, 5, 6, 7, 8, 9, 10 or more specific cleavage agents) in one or more reaction vessels (e.g., sample nucleic acid is treated with each specific cleavage agent in a separate vessel).

Sample nucleic acid also may be exposed to a process that modifies certain nucleotides in the nucleic acid before providing sample nucleic acid for a method described herein. A process that selectively modifies nucleic acid based upon the methylation state of nucleotides therein can be applied to sample nucleic acid. The term "methylation state" as used herein refers to whether a particular nucleotide in a polynucleotide sequence is methylated or not methylated. Methods for modifying a target nucleic acid molecule in a manner that reflects the methylation pattern of the target nucleic acid molecule are known in the art, as exemplified in U.S. Pat. No. 5,786,146 and U.S. patent publications 20030180779 and 20030082600. For example, non-methylated cytosine nucleotides in a nucleic acid can be converted to uracil by bisulfite treatment, which does not modify methylated cytosine. Non-limiting examples of agents that can modify a nucleotide sequence of a nucleic acid include methylmethane sulfonate, ethylmethane sulfonate, diethylsulfate, nitrosoguanidine (N-methyl-N'-nitro-N-nitrosoguanidine), nitrous acid, di-(2-chloroethyl)sulfide, di-(2-chloroethyl)methylamine, 2-aminopurine, t-bromouracil, hydroxylamine, sodium bisulfite, hydrazine, formic acid, sodium nitrite, and 5-methylcytosine DNA glycosylase. In addition, conditions such as high temperature, ultraviolet radiation, x-radiation, can induce changes in the sequence of a nucleic acid molecule.

Sample nucleic acid may be provided in any form useful for conducting a sequence analysis or manufacture process described herein, such as solid or liquid form, for example. In certain embodiments, sample nucleic acid may be provided in a liquid form optionally comprising one or more other components, including without limitation one or more buffers or salts.

Solid Supports and Solid Phase Nucleic Acid

The term "solid support" or "solid phase" as used herein refers to a wide variety of materials including solids, semisolids, gels, films, membranes, meshes, felts, composites, particles, and the like typically used to sequester molecules, and more specifically refers to an insoluble material with which nucleic acid can be associated. A solid support for use with processes described herein sometimes is selected in part according to size: solid supports having a size smaller than the size a microreactor (defined hereafter) sometimes are selected. Examples of solid supports for use with processes described herein include, without limitation, beads (e.g., microbeads, nanobeads) and particles (e.g., microparticles, nanoparticles).

The terms "beads" and "particles" as used herein refer to solid supports suitable for associating with biomolecules, and more specifically nucleic acids. Beads may have a regular (e.g., spheroid, ovoid) or irregular shape (e.g., rough, jagged), and sometimes are non-spherical (e.g., angular, multi-sided). Particles or beads having a nominal, average or mean diameter less than the nominal, average, mean or minimum diameter of a microreactor can be utilized. Particles or beads having a nominal, average or mean diameter of about 1 nanometer to about 500 micrometers can be utilized, such as those having a nominal, mean or average diameter, for example, of about 10 nanometers to about 100 micrometers; about 100 nanometers to about 100 micrometers; about 1 micrometer to about 100 micrometers; about 10 micrometers to about 50 micrometers; about 1, 5, 10, 15, 20, 25, 30, 35, 40, 45, 50, 55, 60, 65, 70, 75, 80, 85, 90, 95, 100, 200, 300, 400, 500, 600, 700, 800 or 900 nanometers; or about 1, 5, 10, 15, 20, 25, 30, 35, 40, 45, 50, 55, 60, 65, 70, 75, 80, 85, 90, 95, 100, 200, 300, 400, 500 micrometers.

A bead or particle can be made of virtually any insoluble or solid material. For example, the bead or particle can comprise or consist essentially of silica gel, glass (e.g. controlled-pore glass (CPG)), nylon, Sephadex®, Sepharose®, cellulose, a metal surface (e.g. steel, gold, silver, aluminum, silicon and copper), a magnetic material, a plastic material (e.g., polyethylene, polypropylene, polyamide, polyester, polyvinylidenedifluoride (PVDF)) and the like. Beads or particles may be swellable (e.g., polymeric beads such as Wang resin) or non-swellable (e.g., CPG). Commercially available examples of beads include without limitation Wang resin, Merrifield resin and Dynabeads®. Beads may also be made as solid particles or particles that contain internal voids.

Solid supports suitable for use with sequence analysis processes described herein often are in association with nucleic acid referred to herein as "solid phase nucleic acid." The term "solid phase nucleic acid" as used herein generally refers to one or more different nucleic acid species in association with a solid support. A solid phase "nucleic acid species" as used herein refers to a first nucleic acid having a nucleotide sequence that differs by one nucleotide base or more from the nucleotide sequence of a second nucleic acid when the nucleotide sequences of the first and second nucleic acids are aligned. Thus one nucleic acid species may differ from a second nucleic acid species by one or more nucleotides when the nucleotide sequences of the first and second nucleic acids are aligned with one another (e.g., about 1, 2, 3, 4, 5, 10, 15, 20, 25, 30, 35, 40, 45, 50, 55, 60, 65, 70, 75, 80, 85, 90, 95, 100 or more than 100 nucleotide differences).

A solid support may be provided in a collection of solid supports. A solid support collection may comprise two or more different solid support species. The term "solid support species" as used herein refers to a solid support in association with one particular solid phase nucleic acid species or a particular combination of different solid phase nucleic acid species. In certain embodiments, a solid support collection comprises 2 to 10,000 solid support species, 10 to 1,000 solid support species or about 2, 3, 4, 5, 6, 7, 8, 9, 10, 15, 20, 25, 30, 35, 40, 45, 50, 55, 60, 65, 70, 75, 80, 85, 90, 95, 100, 200, 300, 400, 500, 600, 700, 800, 900, 1000, 2000, 3000, 4000, 5000, 6000, 7000, 8000, 9000 or 10000 unique solid support species. The solid supports (e.g., beads) in the collection of solid supports may be homogeneous (e.g., all are Wang resin beads) or heterogeneous (e.g., some are Wang resin beads and some are magnetic beads).

Solid phase nucleic acid generally is single-stranded and is of any type suitable for hybridizing sample nucleic acid (e.g., DNA, RNA, analogs thereof (e.g., peptide nucleic acid (PNA)), chimeras thereof (e.g., a single strand comprises RNA bases and DNA bases) and the like). Solid phase nucleic acid is associated with the solid support in any manner suitable for hybridization of solid phase nucleic acid to sample nucleic acid. Solid phase nucleic acid may be in association with a solid support by a covalent linkage or a non-covalent interaction. Non-limiting examples of non-covalent interactions include hydrophobic interactions (e.g., C18 coated solid support and tritylated nucleic acid), polar interactions (e.g., "wetting" association between nucleic acid/polyethylene glycol), pair interactions including without limitation, antibody/antigen, antibody/antibody, antibody/antibody fragment, antibody/antibody receptor, antibody/protein A or protein G, hapten/anti-hapten, biotin/avidin, biotin/streptavidin, folic acid/folate binding protein, vitamin B12/intrinsic factor, nucleic acid/complementary nucleic acid (e.g., DNA, RNA, PNA) and the like.

Solid phase nucleic acid may be associated with a solid support by different methodology, which include, without limitation (i) sequentially synthesizing nucleic acid directly on a solid support, and (ii) synthesizing nucleic acid, providing the nucleic acid in solution phase and linking the nucleic acid to a solid support. Solid phase nucleic acid may be linked covalently at various sites in the nucleic acid to the solid support, such as (i) at a 1', 2', 3', 4' or 5' position of a sugar moiety or (ii) a pyrimidine or purine base moiety, of a terminal or non-terminal nucleotide of the nucleic acid, for example. The 5' terminal nucleotide of the solid phase nucleic acid is linked to the solid support in certain embodiments.

Methods for sequentially synthesizing nucleic acid directly on a solid support are known. For example, the 3' end of nucleic acid can be linked to the solid support (e.g., phosphoramidite method described in Caruthers, Science 230: 281-286 (1985)) or the 5' end of the nucleic acid can be linked to the solid support (e.g., Claeboe et al, Nucleic Acids Res. 31(19): 5685-5691 (2003)). Methods for linking solution phase nucleic acid to a solid support also are known (e.g., U.S. Pat. No. 6,133,436, naming Koster et al. and entitled "Beads bound to a solid support and to nucleic acids" and WO 91/08307, naming Van Ness and entitled "Enhanced capture of target nucleic acid by the use of oligonucleotides covalently attached to polymers"). Examples include, without limitation, thioether linkages (e.g., thiolated nucleic acid); disulfide linkages (e.g., thiol beads, thiolated nucleic acid); amide linkages (e.g., Wang resin, amino-linked nucleic acid); acid labile linkages (e.g., glass beads, tritylated nucleic acid) and the like. Nucleic acid may be linked to a solid support without a linker or with a linker (e.g., S. S. Wong, "Chemistry of Protein Conjugation and Cross-Linking," CRC Press (1991), and G. T. Hermanson, "Bioconjugate Techniques," Academic Press (1995). A homo or hetero-biofunctional linker reagent, can be selected, and examples of linkers include without limitation N-succinimidyl(4-iodoacetyl) aminobenzoate (STAB), dimaleimide, dithio-bis-nitrobenzoic acid (DTNB), N-succinimidyl-S-acetyl-thioacetate (SATA), N-succinimidyl-3-(2-pyridyldithio) propionate (SPDP), succinimidyl 4-(N-maleimidomethyl)cyclohexane-1-carboxylate (SMCC), 6-hydrazinonicotimide (HYNIC), 3-amino-(2-nitrophenyl)propionic acid and the like.

Nucleic acid can be synthesized using standard methods and equipment, such as the ABI®3900 High Throughput DNA Synthesizer and EXPEDITE®8909 Nucleic Acid Synthesizer, both of which are available from Applied Biosystems (Foster City, Calif.). Analogs and derivatives are described in U.S. Pat. Nos. 4,469,863; 5,536,821; 5,541, 306; 5,637,683; 5,637,684; 5,700,922; 5,717,083; 5,719, 262; 5,739,308; 5,773,601; 5,886,165; 5,929,226; 5,977, 296; 6,140,482; WO 00/56746; WO 01/14398, and related publications. Methods for synthesizing nucleic acids comprising such analogs or derivatives are disclosed, for example, in the patent publications cited above and in U.S. Pat. Nos. 5,614,622; 5,739,314; 5,955,599; 5,962,674; 6,117,992; in WO 00/75372 and in related publications. In certain embodiments, analog nucleic acids include inosines, abasic sites, locked nucleic acids, minor groove binders, duplex stabilizers (e.g., acridine, spermidine) and/or other melting temperature modifiers (e.g., target nucleic acid, solid phase nucleic acid, and/or primer nucleic acid may comprise an analog).

The density of solid phase nucleic acid molecules per solid support unit (e.g., one bead) can be selected. A maximum density can be selected that allows for hybridization of sample nucleic acid to solid phase nucleic acid. In certain embodiments, solid phase nucleic acid density per solid support unit (e.g., nucleic acid molecules per bead) is about 5 nucleic acids to about 10,000 nucleic acids per solid support. The density of the solid phase nucleic acid per unit solid support in some embodiments is about 5, 10, 15, 20, 25, 30, 35, 40, 45, 50, 55, 60, 65, 70, 75, 80, 85, 90, 95, 100, 200, 300, 400, 500, 600, 700, 800, 900, 1000, 2000, 3000, 4000, 5000, 6000, 7000, 8000, 9000 or 10000 nucleic acids per solid support. In certain embodiments the density of the solid phase nucleic acid per unit solid support is about 1 to 1 (e.g., one molecule of solid phase nucleic acid to one bead).

In some embodiments, solid phase nucleic acid comprises certain subsequences. One subsequence may be complementary to or substantially complementary to a sample nucleic acid nucleotide subsequence and allows solid phase nucleic acid to hybridize to sample nucleic acid. Such a subsequence (e.g., illustrated in FIGS. 1A-1C) is referred to herein as a "probe" sequence, and a solid support can contain one or more probe sequence species. A "probe sequence species" as used herein refers to a first probe nucleotide sequence that differs by one nucleotide base or more from a second probe nucleotide sequence when the first and second probe nucleotide sequences are aligned. Thus one probe sequence species may differ from a second probe sequence species by one or more nucleotides when the first and second probe sequences are aligned with one another (e.g., about 1, 2, 3, 4, 5, 10, 15, 20, 25, 30, 35, 40, 45, 50, 55, 60, 65, 70, 75, 80, 85, 90, 95, 100 or more than 100 nucleotides that are not identical upon alignment). Alignment techniques and sequence identity assessment methodology are known (e.g., algorithm of Meyers & Miller, CABIOS 4: 11-17 (1989), which has been incorporated into the ALIGN program (version 2.0)).

A probe nucleotide sequence is of a length sufficient to specifically hybridize to a sample nucleic acid nucleotide sequence. In certain embodiments a probe sequence is about 5 to about 100 nucleotides in length, and sometimes is about 5 to about 40 nucleotides in length. Generally, a shorter probe sequence is selected for applications where the target nucleotide sequence is known or partially known and longer probe sequence are selected for applications in which the target nucleotide sequence or portions thereof are not known. In some embodiments, a probe sequence is about 5, 10, 15, 20, 25, 30, 35, 40, 45, 50, 55, 60, 65, 70, 75, 80, 85, 90, 95, 100, 200, 300, 400, 500, 600, 700, 800, 900, 1000, 2000, 3000, 4000 or 5000 nucleotides in length.

In some embodiments solid phase nucleic acid of a solid support species, or a collection of solid support species, may include any number of probe sequence species useful for carrying out sequence analysis processes provided herein. In certain embodiments, one solid support comprises about 10 to about 10,000 unique probe sequences (e.g., about 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, or about 10,000 different probe sequence species); one solid support comprises about 10 to about 1,000 unique probe sequences (e.g., about 10, 20, 30, 40, 50, 60, 70, 80, 90, 100, 200, 300, 400, 500, 600, 700, 800, 900, or about 1,000 different probe sequence species); a collection of solid supports comprises about 10 to about 10,000 unique probe sequences (e.g., about 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, or about 10,000 different probe sequence species); and a collection of solid supports comprises about 10 to about 1,000 unique probe sequences (e.g., about 10, 20, 30, 40, 50, 60, 70, 80, 90, 100, 200, 300, 400, 500, 600, 700, 800, 900, or about 1,000 different probe sequence species). In some embodiments, fewer probe sequence species per solid support or per solid support collection are utilized (e.g., for haplotyping applications) and sometimes greater numbers of probe sequence species per solid support or solid support collection are utilized (e.g., for sequencing applications). In certain embodiments, one solid support, or a collection of solid supports, includes about 5, 10, 15, 20, 25, 30, 35, 40, 45, 50, 55, 60, 65, 70, 75, 80, 85, 90, 95, 100, 200, 300, 400, 500, 600, 700, 800, 900, 1000, 2000, 3000, 4000, 5000, 6000, 7000, 8000, 9000 or 10000 unique probe sequence species. In certain embodiments, solid phase nucleic acid of one solid support species shares only one probe sequence species, and in related collection embodiments, solid phase nucleic acid of each solid support species in the collection shares only one probe sequence species (i.e., one probe sequence species per solid support species).

In certain embodiments, solid phase nucleic acid also may contain an identification sequence (e.g., illustrated in FIGS. 1A-1C), which may be useful in part for constructing partial sequence reads into larger sequence constructions in certain embodiments. An identification sequence can be "unique" for each solid support species, where the term "unique" as used here refers to there being one identification sequence species for each solid support species. An "identification sequence species" as used herein refers to a first identification nucleotide sequence that differs by one nucleotide base or more from a second identification nucleotide sequence when the first and second identification nucleotide sequences are aligned. Thus one identification sequence species may differ from a second identification sequence species by one or more nucleotides when the first and second identification sequences are aligned with one another (e.g., about 1, 2, 3, 4, 5, 10, 15, 20, 25, 30, 35, 40, 45, 50, 55, 60, 65, 70, 75, 80, 85, 90, 95, 100 or more than 100 nucleotides that are not identical upon alignment). An identification sequence may be detected, in some embodiments, by a property selected from the group consisting of size, shape, electrical properties, magnetic properties, optical properties, chemical properties, and the like.

An identification sequence may be of any length suitable for analyzing the nucleotide sequence or partial nucleotide sequence of sample nucleic acid. In some embodiments, an identifier sequence is about 5 to about 50 contiguous nucleotides in length, sometimes about 5 to about 20 nucleotides in length and at times about 10 nucleotides in length. In certain embodiments, an identifier sequence is about 5, 6, 7, 8, 9, 10, 11, 12, 13, 14, 15, 20, 25, 30, 35, 40, 45 or 50 nucleotides in length.

In some embodiments solid phase nucleic acid often includes a primer sequence (Pr), which is also referred to herein as a "primer hybridization sequence." Primer sequence (Pr) can hybridize to a complementary nucleotide sequence in a primer nucleic acid that can be utilized to amplify extended solid phase nucleic acid previously hybridized to a sample nucleic acid. As used herein, the term "primer nucleic acid" refers to a nucleic acid (e.g., naturally occurring or synthetic) that has a nucleic acid sequence complimentary to a primer hybridization sequence, and can hybridize to the primer hybridization sequence under hybridization conditions and can be extended in an amplification process (e.g., primer extension, PCR amplification, and the like). Primer nucleic acids may be of any length suitable for optimized hybridization and may be in the range of about 5 nucleotides to about 5000 nucleotides in length (e.g., about 5 nucleotides, 10, 15, 20, 25, 30, 35, 40, 45, 50, 55, 60, 65, 70, 75, 80, 85, 90, 95, 100, 110, 120, 130, 140, 150, 160, 170, 180, 190, 200, 300, 400, 500, 600, 700, 800, 900, 1000, 1500, 2000, 2500, 3000, 3500, 4000, 4500, or about 5000 nucleotides in length). In some embodiments primer nucleic acids may be modified, which may be effected by a modification process including, without limitation, modification of codons, synthesis using nucleotide analogs, post synthetic modification and the like.

In a collection of solid supports, each solid phase nucleic acid on each solid support species may have a common primer sequence (e.g., all solid support species have the same primer sequence species), in which case the primer sequence is referred to as a "universal" or "common" primer sequence. In certain embodiments, solid phase nucleic acid of a first solid support species in a collection may have a first primer sequence species and solid phase nucleic acid of a second solid support species in the collection may have a second primer sequence species. A "primer sequence species" as used herein refers to a first primer nucleotide sequence that differs by one nucleotide base or more from a second primer nucleotide sequence when the first and second primer nucleotide sequences are aligned. Thus one primer sequence species may differ from a second primer sequence species by one or more nucleotides when the first and second primer sequences are aligned with one another (e.g., about 1, 2, 3, 4, 5, 10, 15, 20, 25, 30, 35, 40, 45, 50, 55, 60, 65, 70, 75, 80, 85, 90, 95, 100 or more than 100 nucleotides that are not identical upon alignment).

Primer hybridization sequence (Pr) can be of a length that allows specific hybridization of a primer under the conditions for primer hybridization, in some embodiments. The length of primer hybridization sequence (Pr) is about 10 to about 100 nucleotides, about 10 to about 50 nucleotides or about 5, 10, 15, 20, 25, 30, 35, 40, 45, 50, 55, 60, 65, 70, 75, 80, 85, 90, 95, or 100 nucleotides in length in certain embodiments. In certain embodiments, sample nucleic acid of a solid support species, or collection of solid supports, includes one or more primer sequence species (e.g., about 1, 2, 3, 4, 5, 10, 15, 20, 25, 30, 35, 40, 45 or 50 unique primer hybridization sequence species). Thus, in certain embodiments, solid phase nucleic acid of a solid support species includes one primer hybridization sequence species, and nucleic acid of a collection of solid supports shares a common primer hybridization sequence species.

Figure 1B:
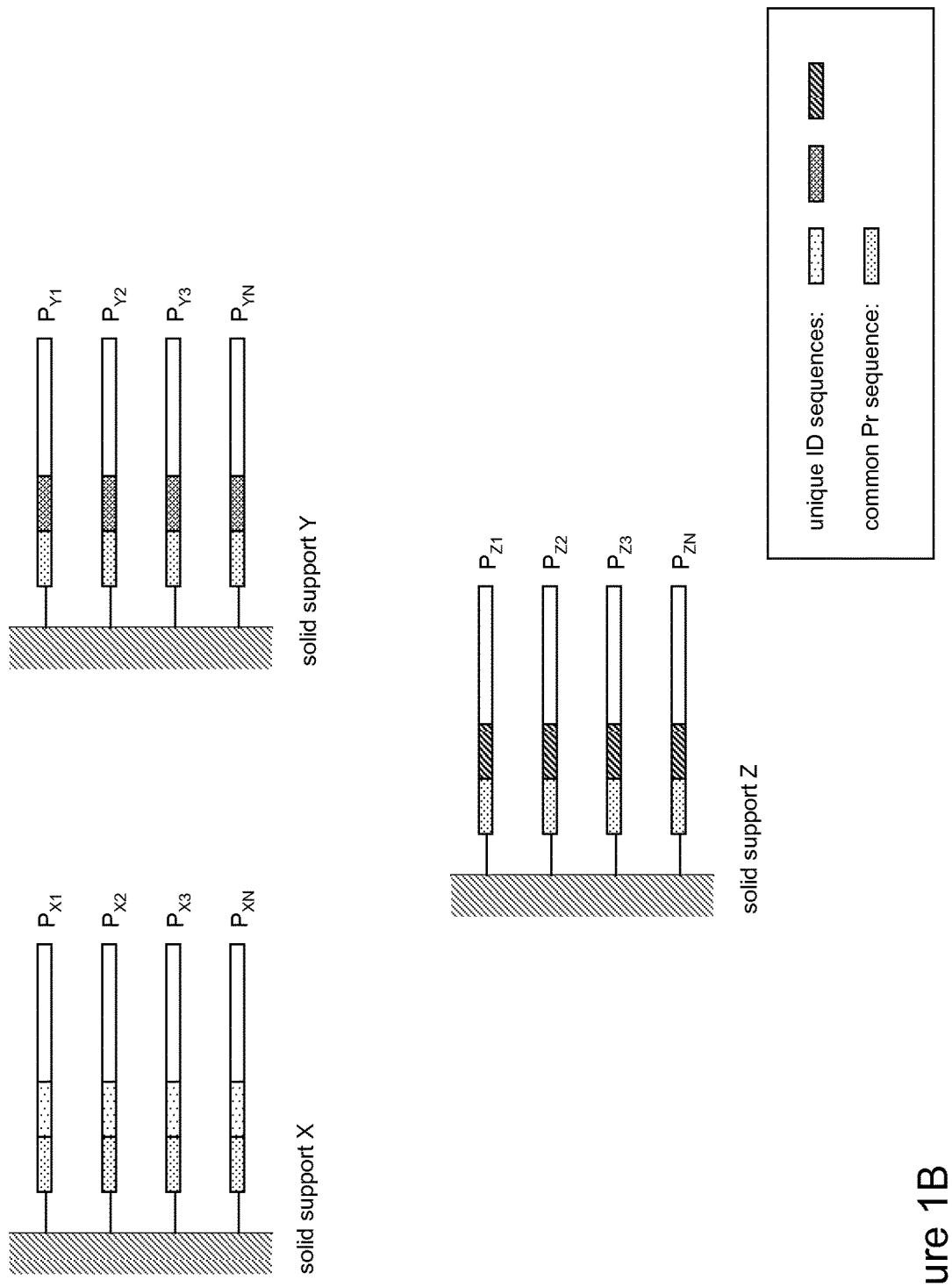
Figure 1C:
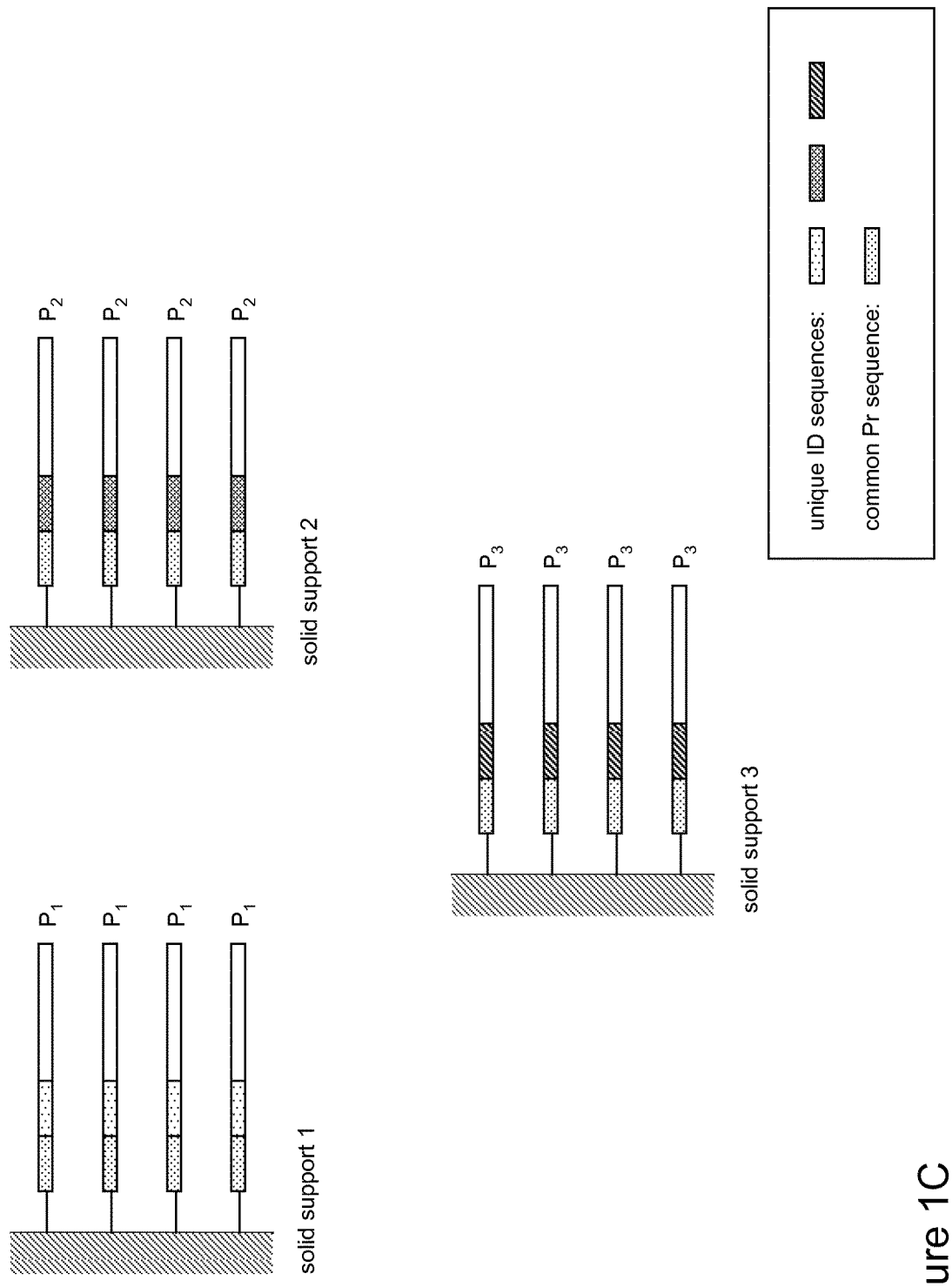

Non-limiting examples of different solid support species, each having probe sequence species, identification sequence species and a primer hybridization sequence species, are shown in FIGS. 1A, 1B and 1C. FIG. 1A shows a solid support species having a particular combination of solid phase nucleic acid differing by probe sequence species $P_1$, $P_2$, $P_3$, ... $P_n$. In FIG. 1A, the probe sequence species are complementary to subsequences in sample nucleic acid (e.g., probe sequence species $P_1$, $P_2$, $P_3$, ... $P_n$ are complementary to sample nucleic acid subsequences 1, 2, 3, ... N, respectively). FIG. 1B shows a collection of three solid support species, where each solid support species includes solid phase nucleic acid having a unique identification sequence and different probe sequence species. In FIG. 1B, solid phase nucleic acid of solid support species X has probe sequence species $P_{X1}$, $P_{X2}$, $P_{X3}$, ... $P_{Xn}$; solid phase nucleic acid of solid support species X has probe sequence species $P_{Y1}$, $P_{Y2}$, $P_{Y3}$, ... $P_{Yn}$; and solid phase nucleic acid of solid support species X has probe sequence species $P_{Z1}$, $P_{Z2}$, $P_{Z3}$, ... $P_{Zn}$. FIG. 1C shows a collection of three solid support species, where each solid support species includes solid phase nucleic acid having a unique identification sequence and the same probe sequence species.

Probe, identification and primer hybridization sequences in solid phase nucleic acid can be arranged in any suitable orientation with respect to one another for performing the methods described herein. Any two of these sequences may be contiguous or may be separated by an intervening sequence of a suitable length (e.g., an intervening sequence of about 1, 2, 3, 4, 5, 10, 15, 20, 25, 30, 35, 40, 45, 50, 55, 60, 65, 70, 75, 80, 85, 90, 95, 100 or more than 100 nucleotides) In certain embodiments, the sequences are contiguous and in the following orientation: 5'-(primer sequence)-(identification sequence)-(probe sequence)-3'.

Solid supports having solid phase nucleic acids may be provided in any convenient form for contacting a sample nucleic acid, such as solid or liquid form, for example. In certain embodiments, a solid support may be provided in a liquid form optionally comprising one or more other components, which include without limitation one or more buffers or salts. Solid supports of a collection may be provided in one container, or may be distributed across multiple containers.

Solid supports may be provided in an array in certain embodiments, or instructions may be provided to arrange solid supports in an array on a substrate. The term "array" as used herein may refer to an arrangement of sample locations on a single two-dimensional solid support, or an arrangement of solid supports across a two-dimensional surface. An array may be of any convenient general shape (e.g., circular, oval, square, rectangular). An array may be referred to as an "X by Y array" for square or rectangular arrays, where the array includes X number of sample locations or solid supports in one dimension and Y number of sample locations or solid supports in a perpendicular dimension. An array may be symmetrical (e.g., a 16 by 16 array) or non-symmetrical (e.g., an 8 by 16 array). An array may include any convenient number of sample locations or solid supports in any suitable arrangement. For example, X or Y independently can be 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 in some embodiments.

An array may contain one solid support species or multiple solid support species from a collection. The array can be arranged on any substrate suitable for sequence analysis or manufacture processes described herein. Examples of substrates include without limitation flat substrates, filter substrates, wafer substrates, etched substrates, substrates having multiple wells or pits (e.g., microliter (about 1 microliter, 5, 10, 15, 20, 25, 30, 35, 40, 45, 50, 55, 60, 65, 70, 75, 80, 85, 90, 95, 100, 110, 120, 130, 140, 150, 160, 170, 180, 190, 200, 300, 400, 500, 600, 700, 800, 900 and up to about 999 microliter volume), nanoliter (1 nanoliter, 5, 10, 15, 20, 25, 30, 35, 40, 45, 50, 55, 60, 65, 70, 75, 80, 85, 90, 95, 100, 110, 120, 130, 140, 150, 160, 170, 180, 190, 200, 300, 400, 500, 600, 700, 800, 900 and up to about 999 nanoliter volume), picoliter (1 picoliter, 5, 10, 15, 20, 25, 30, 35, 40, 45, 50, 55, 60, 65, 70, 75, 80, 85, 90, 95, 100, 110, 120, 130, 140, 150, 160, 170, 180, 190, 200, 300, 400, 500, 600, 700, 800, 900 and up to about 999 picoliter volume) wells or pits; wells having filter bottoms), substrates having one or more channels, substrates having one or more electrodes, and the like, and combinations thereof. Wells or pits of multiple well and pit substrates may contain one or more solid support units (e.g., each unit being a single bead or particle). Substrates can comprise or consist essentially of a suitable material for conducting sequence analysis or manufacture processes described herein, including without limitation, fiber (e.g., fiber filters), glass (e.g., glass surfaces, fiber optic surfaces), metal (e.g., steel, gold, silver, aluminum, silicon and copper; metal coating), plastic (e.g., polyethylene, polypropylene, polyamide, polyvinylidenedifluoride), silicon and the like. In certain embodiments, the array can be a microarray or a nanoarray. A "nanoarray," often is an array in which solid support units are separated by about 0.1 nanometers to about 10 micrometers, for example from about 1 nanometer to about 1 micrometer (e.g. about 0.1 nanometers, 0.5, 1, 2, 3, 4, 5, 10, 20, 30, 40, 50, 60, 70, 80, 90, 100, 200, 300, 400, 500, 600, 700, 800, 900 nanometers, 1 micrometer, 2, 3, 4, 5, 6, 7, 8, 9, and up to about 10 micrometers). A "microarray" is an array in which solid support units are separated by more than 1 micrometer. The density of solid support units on arrays often is at least 100/cm$^2$, and can be 100/cm$^2$ to about 10,000/cm$^2$, 100/cm$^2$ to about 1,000/cm$^2$ or about 150, 200, 300, 400, 500, 600, 700, 800, 900, 1000, 2000, 3000, 4000, 5000, 6000, 7000, 8000, 9000 or 10000 solid support units/cm$^2$.

Single Molecules of Sample Nucleic Acid

In certain methods described herein, sample nucleic acid and solid support are contacted under conditions in which a single molecule of sample nucleic acid hybridizes to a single molecule of a solid support. That is, in some embodiments hybridization conditions can be optimized to allow a single molecule of sample nucleic acid per solid support (e.g. bead or particle), or to allow more than one sample nucleic acid species to hybridize per solid support (e.g., beads or particles are configured to have more than one species of primer sequence, identification sequence, probe sequence, or combinations thereof). In some embodiments a single molecule of nucleic acid sample can be hybridized per solid support under dilute DNA concentration conditions where hybridization of only one molecule of sample nucleic acid per bead is favored. In some embodiments, hybridization conditions can be configured to include only one molecule of sample nucleic acid in the hybridization step. Such conditions can include providing the solid support molecules and a single molecule of sample nucleic acid in a "microreactor" in certain embodiments Such conditions also include providing mixture in which the sample nucleic acid molecule can hybridize to solid phase nucleic acid on the solid support.

As used herein, the term "microreactor" refers to a partitioned space in which a single molecule of sample nucleic acid can hybridize to a solid support molecule. In some embodiments, the microreactor volume is large enough to accommodate one solid support bead in the microreactor and small enough to exclude the presence of two or more beads in the microreactor. Examples of microreactors include without limitation an emulsion globule (described hereafter) and a void in a substrate. A void in a substrate can be a pit, a pore or a well (e.g., microwell, nanowell, picowell, micropore, or nanopore) in a substrate constructed from a solid material useful for containing fluids (e.g., plastic (e.g., polypropylene, polyethylene, polystyrene) or silicon) in certain embodiments. Emulsion globules are partitioned by an immiscible phase as described in greater detail hereafter. A single molecule of sample nucleic acid can be provided in a microreactor by contacting sample nucleic acid molecules with an excess (e.g., molar excess) of solid support molecules. In certain embodiments, the excess amount (e.g., molar amount) of solid support is about 10, 15, 20, 25, 30, 35, 40, 45, 50, 55, 60, 65, 70, 75, 80, 85, 90, 95, 100, 150, 200, 300, 400, 500, 600, 700, 800, 900, 1000, 2000, 3000, 4000, 5000, 6000, 7000, 8000, 9000, 10000 times, or more, the amount of sample nucleic acid.

The term "emulsion" as used herein refers to a mixture of two immiscible and unblendable substances, in which one substance (the dispersed phase) often is dispersed in the other substance (the continuous phase). The dispersed phase can be an aqueous solution (i.e., a solution comprising water) in certain embodiments. In some embodiments, the dispersed phase is composed predominantly of water (e.g., greater than 70%, greater than 75%, greater than 80%, greater than 85%, greater than 90%, greater than 95%, greater than 97%, greater than 98% and greater than 99% water (by weight)). Each discrete portion of a dispersed phase, such as an aqueous dispersed phase, is referred to herein as a "globule" or "microreactor." A globule sometimes may be spheroidal, substantially spheroidal or semi-spheroidal in shape, in certain embodiments.

The terms "emulsion apparatus" and "emulsion component(s)" as used herein refer to apparatus and components that can be used to prepare an emulsion. Non-limiting examples of emulsion apparatus include without limitation counter-flow, cross-current, rotating drum and membrane apparatus suitable for use to prepare an emulsion. An emulsion component forms the continuous phase of an emulsion in certain embodiments, and includes without limitation a substance immiscible with water, such as a component comprising or consisting essentially of an oil (e.g., a heat-stable, biocompatible oil (e.g., light mineral oil)). A biocompatible emulsion stabilizer can be utilized as an emulsion component. Emulsion stabilizers include without limitation Atlox 4912, Span 80 and other biocompatible surfactants.

In some embodiments, components useful for biological reactions can be included in the dispersed phase. Globules of the emulsion can include (i) a solid support unit (e.g., one bead or one particle); (ii) sample nucleic acid molecule; and (iii) a sufficient amount of extension agents to elongate solid phase nucleic acid and amplify the elongated solid phase nucleic acid (e.g., extension nucleotides, polymerase, primer). Inactive globules in the emulsion may include a subset of these components (e.g., solid support and extension reagents and no sample nucleic acid) and some can be empty (i.e., some globules will include no solid support, no sample nucleic acid and no extension agents).

Emulsions may be prepared using suitable methods (e.g., Nakano et al. "Single-molecule PCR using water-in-oil emulsion;" Journal of Biotechnology 102 (2003) 117-124). Emulsification methods include without limitation adjuvant methods, counter-flow methods, cross-current methods, rotating drum methods, membrane methods, and the like. In certain embodiments, an aqueous reaction mixture containing a solid support (hereafter the "reaction mixture") is prepared and then added to a biocompatible oil. The reaction mixture can contain (i) a solid support or solid support collection; (ii) sample nucleic acid; (iii) extension agents and (iv) one or more primers in certain embodiments. Each of these components can be mixed in any suitable order to prepare the reaction mixture. In certain embodiments, the reaction mixture may be added dropwise into a spinning mixture of biocompatible oil (e.g., light mineral oil (Sigma)) and allowed to emulsify. In some embodiments, the reaction mixture may be added dropwise into a cross-flow of biocompatible oil. The size of aqueous globules in the emulsion can be adjusted, such as by varying the flow rate and speed at which the components are added to one another, for example.

The size of emulsion globules can be selected based on two competing factors in certain embodiments: (i) globules are sufficiently large to encompass one solid support molecule, one sample nucleic acid molecule, and sufficient extension agents for the degree of elongation and amplification required; and (ii) globules are sufficiently small so that a population of globules can be amplified by conventional laboratory equipment (e.g., thermocycling equipment, test tubes, incubators and the like). Globules in the emulsion can have a nominal, mean or average diameter of about 5 microns to about 500 microns, about 10 microns to about 350 microns, about 50 to 250 microns, about 100 microns to about 200 microns, or about 5, 10, 15, 20, 25, 30, 35, 40, 45, 50, 55, 60, 65, 70, 75, 80, 85, 90, 95, 100, 200, 300, 400 or 500 microns in certain embodiments.

Sample nucleic acid, solid support(s), extension agents and emulsion component(s) can be mixed in any suitable manner and in any suitable ratios to carry out the methods described herein, including without limitation, manual and automated means (e.g. biological workstations). Any suitable ratio of solid support to sample nucleic acid can be utilized to obtain globules having one sample nucleic acid per solid support unit, and in some embodiments, a ratio of solid support concentration to sample nucleic acid concentration is equal to or greater than 10:1, and in some embodiments, the ratio is about 15, 20, 25, 30, 35, 40, 45, 50, 55, 60, 65, 70, 75, 80, 85, 90, 95, 100, 200, 300, 400, 500, 600, 700, 800, 900, 1000, 2000, 3000, 4000, 5000, 6000, 7000, 8000, 9000 or 10000, to 1. In some embodiments, (a) sample nucleic acid may be contacted with a solid support or collection of solid supports under conditions in which sample nucleic acid can hybridize to solid phase nucleic acid, (b) the mixture of (a) can be contacted with extension agents, and (c) the mixture of (b) can be emulsified with a solution immiscible with water (e.g., a biocompatible oil). In certain embodiments, an emulsion can be prepared contemporaneously with contacting the mixture with extension agents.

Hybridization conditions that allow for hybridization of sample nucleic acid to solid phase nucleic acid are known. Non-limiting examples of hybridization conditions include without limitation, hybridization in 6× sodium chloride/sodium citrate (SSC) at about 45° C., followed by one or more washes in 0.2×SSC, 0.1% SDS at 50° C. Another example of stringent hybridization conditions are hybridization in 6× sodium chloride/sodium citrate (SSC) at about 45° C., followed by one or more washes in 0.2×SSC, 0.1% SDS at 55° C., or 6× sodium chloride/sodium citrate (SSC) at about 45° C., followed by one or more washes in 0.2×SSC, 0.1% SDS at 60° C. Stringent hybridization conditions sometimes are hybridization in 6× sodium chloride/sodium citrate (SSC) at about 45° C., followed by one or more washes in 0.2×SSC, 0.1% SDS at 65° C. Stringency conditions at times are 0.5M sodium phosphate, 7% SDS at 65° C., followed by one or more washes at 0.2×SSC, 1% SDS at 65° C. Hybridization conditions also are described for example in WO 91/08307, entitled "Enhanced capture of target nucleic acid by the use of oligonucleotides covalently attached to polymers," naming Van Ness, and "Nucleic Acid Hybridization, A Practical Approach," Ed. Hames and Higgens, IRL Press, 1985.

Amplification

The term "extension agents" and "extension reagents" as used herein refer to components useful for extending a nucleic acid. Conditions under which nucleic acids can be extended and/or amplified by such agents are known. In certain embodiments, extension agents may include one or more of the following: extension nucleotides, a polymerase and a primer that can hybridize to a primer sequence in solid phase nucleic acid. Extension nucleotides include, in some embodiments, naturally occurring deoxynucleotide triphosphates (dATP, dTTP, dCTP, dGTP, dUTP) and non-naturally occurring nucleotides or nucleotide analogs, such as analogs containing a detectable label (e.g., fluorescent or colormetric label), for example. Polymerases include, in some embodiments, polymerases for thermocycle amplification (e.g., Taq DNA Polymerase; Q-Bio™ Taq DNA Polymerase (recombinant truncated form of Taq DNA Polymerase lacking 5'-3'exo activity); SurePrime™ Polymerase (chemically modified Taq DNA polymerase for "hot start" PCR); Arrow™ Taq DNA Polymerase (high sensitivity and long template amplification)) and polymerases for thermostable amplification (e.g., RNA polymerase for transcription-mediated amplification (TMA) described at World Wide Web URL "gen-probe.com/pdfs/tma_whiteppr.pdf"). Other enzyme components can be added, such as reverse transcriptase for TMA reactions, for example.

A primer nucleic acid may be of any length suitable for hybridizing to a primer hybridization sequence in solid phase nucleic acid and performing sequence analysis processes described herein. A primer in some embodiments may be about 10 to about 100 nucleotides, about 10 to about 70 nucleotides, about 10 to about 50 nucleotides, about 15 to about 30 nucleotides, or about 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95 or 100 nucleotides in length. A primer may be composed of naturally occurring and/or non-naturally occurring nucleotides, or a mixture thereof. A primer often includes a nucleotide subsequence that is complementary to a solid phase nucleic acid primer hybridization sequence or substantially complementary to a solid phase nucleic acid primer hybridization sequence (e.g., about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater than 99% identical to the primer hybridization sequence complement when aligned). A primer may contain a nucleotide subsequence not complementary to or not substantially complementary to a solid phase nucleic acid primer hybridization sequence (e.g., at the 3' or 5' end of the nucleotide subsequence in the primer complementary to or substantially complementary to the solid phase primer hybridization sequence). A primer in certain embodiments, may contain a detectable molecule (e.g., a fluorophore, radioisotope, colormetric agent, particle, enzyme and the like).

In processes provided herein, components of a microreactor may be contacted with extension agents under amplification conditions. The term "amplification conditions" as used herein refers to thermocycle and thermostable conditions that can facilitate amplification of a nucleic acid. Thermostable conditions can be maintained and the type and amount of amplification generally is dependent on the extension agents added to the mixture (e.g., primers, RNA polymerase and reverse transcriptase components for TMA (described above)). Thermocycle conditions generally involve repeating temperature fluctuation cycles, and apparatus for effecting such cycles are available. A non-limiting example of thermocycle conditions is treating the sample at 95° C. for 5 minutes; repeating forty-five cycles of 95° C. for 1 minute, 59° C. for 1 minute, 10 seconds, and 72° C. for 1 minute 30 seconds; and then treating the sample at 72° C. for 5 minutes. Multiple cycles frequently are performed using a commercially available thermal cycler (e.g., Applied Biosystems 2720 thermal cycler apparatus). In certain embodiments, an emulsified mixture may be subjected to thermocycle conditions for linear amplification using one primer that hybridizes to a solid phase nucleic acid primer hybridization sequence.

An amplification product for signal analysis can be of any length suitable for sequence analysis methods. In certain embodiments, an amplification product can be about 5 to about 10,000 nucleotides in length, about 10 to about 1,000 nucleotides in length, about 10 to about 100 nucleotides in length, about 10 to about 50 nucleotides in length, or about 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 200, 300, 400, 500, 600, 700, 800, 900, 1000, 2000, 3000, 4000, 5000, 6000, 7000, 8000, 9000 or 10000 nucleotides in length. An amplification product may include naturally occurring nucleotides, non-naturally occurring nucleotides, nucleotide analogs and the like and combinations of the foregoing. An amplification product often has a nucleotide sequence that is identical to or substantially identical to a sample nucleic acid nucleotide sequence or complement thereof. A "substantially identical" nucleotide sequence in an amplification product will generally have a high degree of sequence identity to the sample nucleotide sequence or complement thereof (e.g., about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater than 99% sequence identity), and variations often will be a result of infidelity of the polymerase used for extension and/or amplification.

Amplification products (e.g., amplification products of FIG. 2) may be contacted with additional amplification agents and/or subjected to further amplification conditions in certain embodiments, such as exponential amplification that involves more than one primer and thermocylcing, for example. Any suitable amplification process may utilized, such as amplification methods for use with the pyrosequencing and sequencing by ligation methodologies described hereafter, for example, in certain embodiments.

Figure 2:
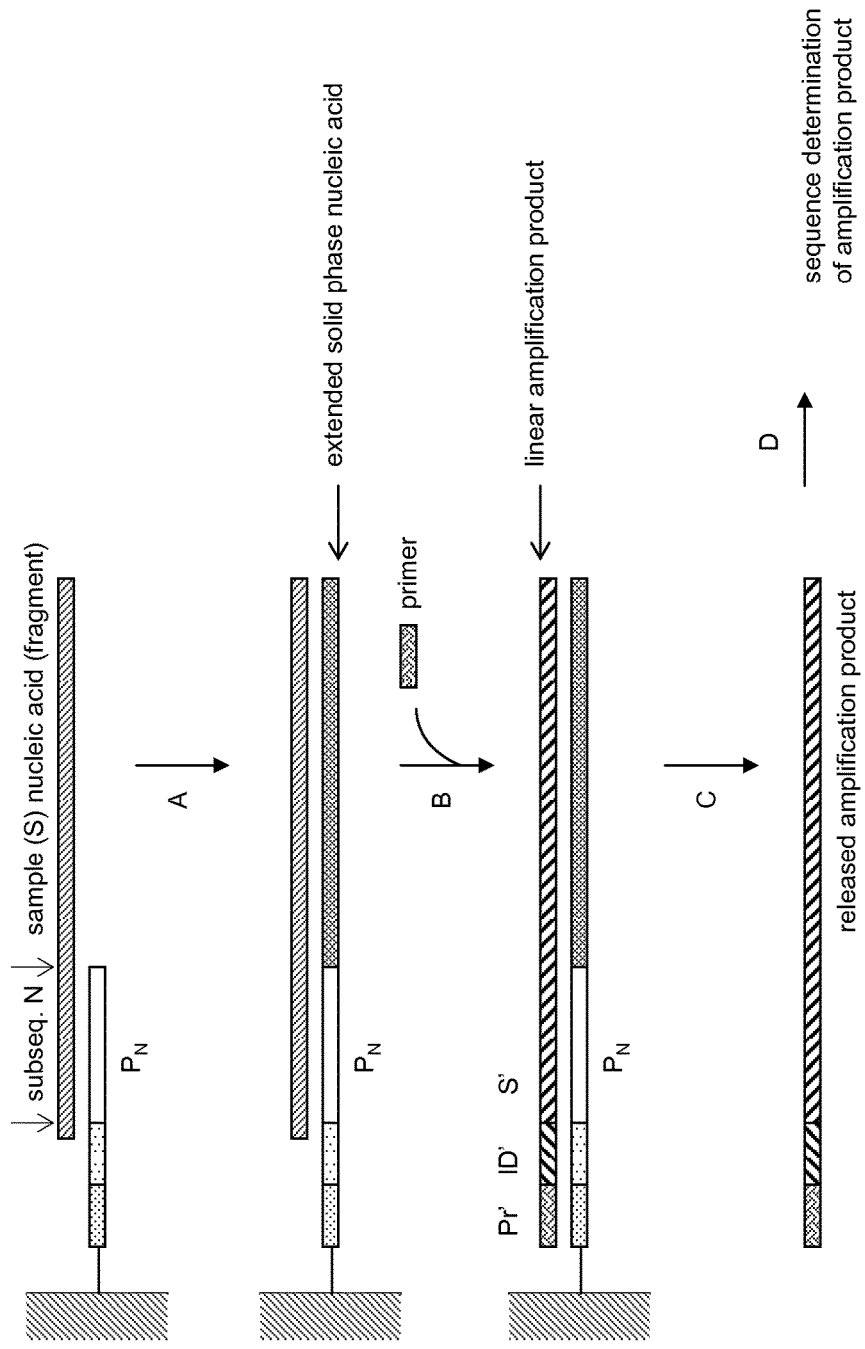
FIG. 2 shows a representative process for generating nucleic acids having a nucleotide sequence complementary to a target nucleotide sequence.

In certain embodiments, linear amplification products are analyzed directly without further amplification by another process (e.g., linear amplification products of FIG. 2 are not amplified further by an exponential amplification process). In some embodiments, sample nucleic acid, extended solid phase nucleic acid and/or amplification products are not ligated to one or more heterologous nucleic acids (e.g., in contrast to methods described in U.S. Patent Application Publication No. 20040110191, entitled "Comparative analysis of nucleic acids using population tagging," naming Winkler et al.; U.S. Patent Application Publication No. 20050214825, entitled "Multiplex sample analysis on universal arrays," naming Stuelpnagel; and Nakano et al. "Single-molecule PCR using water-in-oil emulsion"; Journal of Biotechnology 102 (2003) 117-124), such as heterologous nucleic acids that hybridize to an amplification primer. Nucleic acid sequences of amplification products that are not further amplified may be analyzed by a direct sequence analysis method (e.g., single-molecule sequencing methodology described hereafter).

Amplification products may be released from a solid support in certain embodiments. A suitable method for releasing an amplification product from a solid support can be utilized, such as by heating the solid support (e.g., heating to about 95 degrees C.), exposing the solid support to an amount of a chaeotrope (e.g., guanidinium HCL) sufficient to release the amplified nucleic acid, and the like, for example, in some embodiments.

FIG. 2 illustrates a process embodiment in which a sample nucleic acid molecule (S), provided as nucleic acid fragments in some embodiments, can be hybridized to a solid support described herein. Sample nucleic acid molecule (S) may include a nucleotide sequence (i.e., subseq.N) that hybridizes to a complementary probe sequence ($P_N$) of the solid phase nucleic acid. Solid phase nucleic acid hybridized to sample nucleic acid (S) can be extended (e.g., illustrated in FIG. 2 as A) and "extended solid phase nucleic acid" is generated. In some embodiments extended solid phase nucleic acid may include a nucleotide subsequence complementary to a target nucleotide sequence in the sample nucleic acid molecule. Extended solid phase nucleic acid may be amplified by hybridizing primer (Pr'), which is complementary to primer sequence (Pr) of the extended solid phase nucleic acid, in the presence of amplification/extension reagents (illustrated in FIG. 2 as B). The hybridized primer is extended thereby generating an amplification product. The amplification product contains the primer nucleotide sequence (Pr'), a nucleotide sequence complementary to the identification sequence in solid phase nucleic acid, and a nucleotide sequence identical to or substantially identical to a target nucleotide sequence in the sample nucleic acid molecule. This linear amplification product can be released from the solid support for sequence analysis (e.g., illustrated in FIG. 2 as C).

Sequence Analysis

Amplification products generated by processes described herein may be subject to sequence analysis. The term "sequence analysis" as used herein refers to determining a nucleotide sequence of an amplification product. The entire sequence or a partial sequence of an amplification product can be determined, and the determined nucleotide sequence is referred to herein as a "read." A read may be obtained with or without further amplification of amplification products resulting from extension of a primer that hybridizes to the primer hybridization sequence in solid phase nucleic acid. For example, linear amplification products may be analyzed directly without further amplification in some embodiments (e.g., by using single-molecule sequencing methodology (described in greater detail hereafter)). In certain embodiments, linear amplification products may be subject to further amplification and then analyzed (e.g., using sequencing by ligation or pyrosequencing methodology (described in greater detail hereafter)). Reads may be subject to different types of sequence analysis.

In certain sequence analysis embodiments, reads may be used to construct a larger nucleotide sequence, which can be facilitated by identifying overlapping sequences in different reads and by using identification sequences in the reads. Such sequence analysis methods and software for constructing larger sequences from reads are known (e.g., Venter et al., Science 291: 1304-1351 (2001)). Specific reads, partial nucleotide sequence constructs, and full nucleotide sequence constructs may be compared between nucleotide sequences within a sample nucleic acid (i.e., internal comparison) or may be compared with a reference sequence (i.e., reference comparison) in certain sequence analysis embodiments. Internal comparisons sometimes are performed in situations where a sample nucleic acid is prepared from multiple samples or from a single sample source that contains sequence variations. Reference comparisons sometimes are performed when a reference nucleotide sequence is known and an objective is to determine whether a sample nucleic acid contains a nucleotide sequence that is substantially similar or the same, or different, than a reference nucleotide sequence. Sequence analysis is facilitated by sequence analysis apparatus and components.

In some embodiments target nucleic acid species can be further analyzed by nucleotide sequencing. Any suitable sequencing method can be utilized. In some embodiments, nucleotide sequencing may be by single nucleotide sequencing methods and processes. Single nucleotide sequencing methods involve contacting sample nucleic acid and solid support under conditions in which a single molecule of sample nucleic acid hybridizes to a single molecule of a solid support. Such conditions can include providing the solid support molecules and a single molecule of sample nucleic acid in a "microreactor." Such conditions also can include providing a mixture in which the sample nucleic acid molecule can hybridize to solid phase nucleic acid on the solid support. Single nucleotide sequencing methods useful in the embodiments described herein are described in U.S. Provisional Patent Application Ser. No. 61/021,871 filed Jan. 17, 2008, and incorporated herein by reference, in its entirety.

The terms "sequence analysis apparatus" and "sequence analysis component(s)" used herein refer to apparatus, and one or more components used in conjunction with such apparatus, that can be used to determine a nucleotide sequence from amplification products resulting from processes described herein (e.g., linear and/or exponential amplification products). Non-limiting examples of current sequence analysis apparatus and components include, without limitation, systems that involve (i) sequencing by ligation of dye-modified probes (e.g., including cyclic ligation and cleavage), (ii) pyrosequencing, and (iii) single-molecule sequencing. An amplification product generated by a process described herein (e.g., released linear amplification product in FIG. 2) can be considered a "study nucleic acid" for purposes of analyzing a nucleotide sequence by such sequence analysis apparatus and components. Examples of sequencing platforms include, without limitation, the 454 platform (Roche) (Margulies, M. et al. 2005 Nature 437, 376-380), Illumina Genomic Analyzer (or Solexa platform) or SOLID System (Applied Biosystems) or the Helicos True Single Molecule DNA sequencing technology (Harris T D et al. 2008 Science, 320, 106-109), the single molecule, real-time (SMRT™) technology of Pacific Biosciences, and nanopore sequencing (Soni G V and Meller A. 2007 Clin Chem 53: 1996-2001). Such platforms allow sequencing of many nucleic acid molecules isolated from a specimen at high orders of multiplexing in a parallel manner (Dear Brief Funct Genomic Proteomic 2003; 1: 397-416). Each of these platforms allow sequencing of clonally expanded or non-amplified single molecules of nucleic acid fragments.

Sequencing by ligation is another nucleic acid sequencing method. Sequencing by ligation relies on the sensitivity of DNA ligase to base-pairing mismatch. DNA ligase joins together ends of DNA that are correctly base paired. Combining the ability of DNA ligase to join together only correctly base paired DNA ends, with mixed pools of fluorescently labeled oligonucleotides or primers, enables sequence determination by fluorescence detection. Longer sequence reads may be obtained by including primers containing cleavable linkages that can be cleaved after label identification. Cleavage at the linker removes the label and regenerates the 5' phosphate on the end of the ligated primer, preparing the primer for another round of ligation. In some embodiments primers may be labeled one or more fluorescent labels (e.g., one fluorescent label; 2, 3, or 4 fluorescent labels).

An example of a system that can be used based on sequencing by ligation generally involves the following steps. Clonal bead populations can be prepared in emulsion microreactors containing study nucleic acid ("template"), amplification reaction components, beads and primers. After amplification, templates are denatured and bead enrichment is performed to separate beads with extended templates from undesired beads (e.g., beads with no extended templates). The template on the selected beads undergoes a 3' modification to allow covalent bonding to the slide, and modified beads can be deposited onto a glass slide. Deposition chambers offer the ability to segment a slide into one, four or eight chambers during the bead loading process. For sequence analysis, primers hybridize to the adapter sequence. A set of four color dye-labeled probes compete for ligation to the sequencing primer. Specificity of probe ligation is achieved by interrogating every 4th and 5th base during the ligation series. Five to seven rounds of ligation, detection and cleavage record the color at every 5th position with the number of rounds determined by the type of library used. Following each round of ligation, a new complimentary primer offset by one base in the 5' direction is laid down for another series of ligations. Primer reset and ligation rounds (5-7 ligation cycles per round) are repeated sequentially five times to generate 25-35 base pairs of sequence for a single tag. With mate-paired sequencing, this process is repeated for a second tag. Such a system can be used to exponentially amplify amplification products generated by a process described herein, e.g., by ligating a heterologous nucleic acid to the first amplification product generated by a process described herein (e.g., a linear amplification product of FIG. 2) and performing emulsion amplification using the same or a different solid support originally used to generate the first amplification product. Such a system also may be used to analyze amplification products directly generated by a process described herein (e.g., a linear amplification product of FIG. 2) by bypassing an exponential amplification process and directly sorting the solid supports described herein on the glass slide.

Pyrosequencing is a nucleic acid sequencing method based on sequencing by synthesis, which relies on detection of a pyrophosphate released on nucleotide incorporation. Generally, sequencing by synthesis involves synthesizing, one nucleotide at a time, a DNA strand complimentary to the strand whose sequence is being sought. Study nucleic acids may be immobilized to a solid support, hybridized with a sequencing primer, incubated with DNA polymerase, ATP sulfurylase, luciferase, apyrase, adenosine 5' phosphsulfate and luciferin. Nucleotide solutions are sequentially added and removed. Correct incorporation of a nucleotide releases a pyrophosphate, which interacts with ATP sulfurylase and produces ATP in the presence of adenosine 5' phosphsulfate, fueling the luciferin reaction, which produces a chemiluminescent signal allowing sequence determination.

An example of a system that can be used based on pyrosequencing generally involves the following steps: ligating an adaptor nucleic acid to a study nucleic acid and hybridizing the study nucleic acid to a bead; amplifying a nucleotide sequence in the study nucleic acid in an emulsion; sorting beads using a picoliter multiwell solid support; and sequencing amplified nucleotide sequences by pyrosequencing methodology (e.g., Nakano et al. "Single-molecule PCR using water-in-oil emulsion;" Journal of Biotechnology 102 (2003) 117-124). Such a system can be used to exponentially amplify amplification products generated by a process described herein, e.g., by ligating a heterologous nucleic acid to the first amplification product generated by a process described herein (e.g., a linear amplification product of FIG. 2) and performing emulsion amplification using the same or a different solid support originally used to generate the first amplification product. Such a system also may be used to analyze amplification products directly generated by a process described herein (e.g., a linear amplification product of FIG. 2) by bypassing an exponential amplification process and directly sorting solid supports described herein on the picoliter multiwell support.

Certain single-molecule sequencing embodiments are based on the principal of sequencing by synthesis, and utilize single-pair Fluorescence Resonance Energy Transfer (single pair FRET) as a mechanism by which photons are emitted as a result of successful nucleotide incorporation. The emitted photons often are detected using intensified or high sensitivity cooled charge-couple-devices in conjunction with total internal reflection microscopy (TIRM). Photons are only emitted when the introduced reaction solution contains the correct nucleotide for incorporation into the growing nucleic acid chain that is synthesized as a result of the sequencing process. In FRET based single-molecule sequencing, energy is transferred between two fluorescent dyes, sometimes polymethine cyanine dyes Cy3 and Cy5, through long-range dipole interactions. The donor is excited at its specific excitation wavelength and the excited state energy is transferred, non-radiatively to the acceptor dye, which in turn becomes excited. The acceptor dye eventually returns to the ground state by radiative emission of a photon. The two dyes used in the energy transfer process represent the "single pair", in single pair FRET. Cy3 often is used as the donor fluorophore and often is incorporated as the first labeled nucleotide. Cy5 often is used as the acceptor fluorophore and is used as the nucleotide label for successive nucleotide additions after incorporation of a first Cy3 labeled nucleotide. The fluorophores generally are within 10 nanometers of each for energy transfer to occur successfully.

An example of a system that can be used based on single-molecule sequencing generally involves hybridizing a primer to a study nucleic acid to generate a complex; associating the complex with a solid phase; iteratively extending the primer by a nucleotide tagged with a fluorescent molecule; and capturing an image of fluorescence resonance energy transfer signals after each iteration (e.g., U.S. Pat. No. 7,169,314; Braslaysky et al., PNAS 100(7): 3960-3964 (2003)). Such a system can be used to directly sequence amplification products generated by processes described herein (e.g., released linear amplification product in FIG. 2). In some embodiments the released linear amplification product can be hybridized to a primer that contains sequences complementary to immobilized capture sequences present on a solid support, a bead or glass slide for example. Hybridization of the primer—released linear amplification product complexes with the immobilized capture sequences, immobilizes released linear amplification products to solid supports for single pair FRET based sequencing by synthesis. The primer often is fluorescent, so that an initial reference image of the surface of the slide with immobilized nucleic acids can be generated. The initial reference image is useful for determining locations at which true nucleotide incorporation is occurring. Fluorescence signals detected in array locations not initially identified in the "primer only" reference image are discarded as non-specific fluorescence. Following immobilization of the primer—released linear amplification product complexes, the bound nucleic acids often are sequenced in parallel by the iterative steps of, a) polymerase extension in the presence of one fluorescently labeled nucleotide, b) detection of fluorescence using appropriate microscopy, TIRM for example, c) removal of fluorescent nucleotide, and d) return to step a with a different fluorescently labeled nucleotide.

Nucleotide sequence analysis can include, in some embodiments, fixing nucleotide sequence information in tangible or electronic form. Nucleotide sequence information includes without limitation one or more nucleotide sequences (e.g., string(s) of nucleotide bases, full sequences, partial sequences), information pertaining to process(es) used to obtain a sample nucleotide sequence, information pertaining to process(es) used to obtain a sample nucleic acid from a sample, and information pertaining to the sample(s) from which sample nucleic was obtained (e.g., patient information, population information, location of a sample source). Nucleotide sequence information can be fixed in any tangible or electronic form, including without limitation a physical medium (e.g., paper and the like) or a computer readable medium (e.g., optical and/or magnetic storage or transmission medium, floppy disk, hard disk, random access memory, computer processing unit, facsimile signal, satellite signal, internet, world wide web and the like). Nucleotide sequence information may be fixed in an official or unofficial record (e.g., patient record, insurance record, laboratory notebook, government record (e.g., Center of Disease Control record) and the like). Sequence information sometimes is stored and organized in a database. In certain embodiments, sequence information may be transferred from one location to another using a physical medium or electronic medium (e.g., transmission from a site in China to a site in the United States or a territory thereof).

Kits

Kits often comprise one or more containers that contain one or more components described herein. A kit comprises one or more components in any number of separate containers, packets, tubes, vials, multiwell plates and the like, or components may be combined in various combinations in such containers. One or more of the following components, for example, may be included in a kit: (i) a solid support having solid phase nucleic acid; (i) a collection of solid supports having solid phase nucleic acid; (iii) nucleic acid that can be associated with a solid support to generate a solid support having solid phase nucleic acid; (iv) one or more agents that can be used to associate nucleic acid with a solid support to generate a solid support having solid phase nucleic acid; (v) nucleic acid-free solid support(s); (vi) one or more extension agents; (vii) one or more components; (viii) emulsion apparatus and/or emulsion component(s); (ix) nucleic acid amplification apparatus and/or nucleic acid amplification component(s); (x) sequence analysis apparatus and/or sequence analysis component(s); (xi) a substrate containing microreactor wells or pits and (xii) nucleotide sequence analysis software.

A kit sometimes is utilized in conjunction with a process, and can include instructions for performing one or more processes and/or a description of one or more compositions. A kit may be utilized to carry out a process (e.g., using a solid support) described herein. Instructions and/or descriptions may be in tangible form (e.g., paper and the like) or electronic form (e.g., computer readable file on a tangle medium (e.g., compact disc) and the like) and may be included in a kit insert. A kit also may include a written description of an internet location that provides such instructions or descriptions.

Applications

Processes and solid supports provided herein are useful for several types of analyses, non-limiting examples of which are described hereafter.

1. Microbial Identification

A strain or strains of microorganisms can be identified using processes and solid supports described herein. The microorganism(s) are selected from a variety of organisms including, but not limited to, bacteria, fungi, protozoa, ciliates, and viruses. The microorganisms are not limited to a particular genus, species, strain, subtype or serotype. The microorganisms can be identified by determining sequence variations in a target microorganism sequence relative to one or more reference sequences or samples. The reference sequence(s) can be obtained from, for example, other microorganisms from the same or different genus, species strain or serotype, or from a host prokaryotic or eukaryotic organism.

Identification and typing of pathogens (e.g., bacterial or viral) is critical in the clinical management of infectious diseases. Precise identity of a microbe is used not only to differentiate a disease state from a healthy state, but is also fundamental to determining the source of the infection and its spread and whether and which antibiotics or other antimicrobial therapies are most suitable for treatment. In addition treatment can be monitored. Traditional methods of pathogen typing have used a variety of phenotypic features, including growth characteristics, color, cell or colony morphology, antibiotic susceptibility, staining, smell, serotyping and reactivity with specific antibodies to identify microbes (e.g., bacteria). All of these methods require culture of the suspected pathogen, which suffers from a number of serious shortcomings, including high material and labor costs, danger of worker exposure, false positives due to mishandling and false negatives due to low numbers of viable cells or due to the fastidious culture requirements of many pathogens. In addition, culture methods require a relatively long time to achieve diagnosis, and because of the potentially life-threatening nature of such infections, antimicrobial therapy is often started before the results can be obtained. Some organisms cannot be maintained in culture or exhibit prohibitively slow growth rates (e.g., up to 6-8 weeks for *Mycobacterium tuberculosis*).

In many cases, the pathogens are present in minor amounts and/or are very similar to the organisms that make up the normal flora, and can be indistinguishable from the innocuous strains by the methods cited above. In these cases, determination of the presence of the pathogenic strain can require the higher resolution afforded by the molecular typing methods provided herein. For example, in some embodiments PCR amplification of a target nucleic acid sequence followed by specific cleavage (e.g., base-specific), followed by matrix-assisted laser desorption/ionization time-of-flight mass spectrometry, followed by screening for sequence variations as provided herein, allows reliable discrimination of sequences differing by only one nucleotide and combines the discriminatory power of the sequence information generated with the speed of MALDI-TOF MS.

Thus, provided herein is a method for detecting a microbial nucleotide sequence in a sample, which comprises (a) providing a sample nucleic acid (e.g., taken from a subject); (b) preparing a mixture of the sample nucleic acid with a solid support described herein having solid phase nucleic acid under conditions in which a single molecule of the sample nucleic acid hybridizes to a solid support molecule; (c) contacting the mixture with extension agents under conditions in which solid phase nucleic acid hybridized to sample nucleic acid is extended; (d) amplifying extended solid phase nucleic acid; (e) analyzing the sequence of the amplified nucleic acid of (d); and (f) based on a sequence determined in (e) identifying the presence or absence of the microbial nucleotide sequence in the sample nucleic acid. Part (d) is optional in certain embodiments: the extended solid phase nucleic acid of (c) may be analyzed by sequencing (e), without amplification (d), using sequencing by synthesis methods described above, for example.

2. Detection of Sequence Variations

Genomic bases of disease and markers thereof can be detected using the processes and solid supports herein. The sequence variation candidates identified by the methods provided herein include sequences containing sequence variations that are polymorphisms. Polymorphisms include both naturally occurring, somatic sequence variations and those arising from mutation. Polymorphisms include but are not limited to: sequence microvariants where one or more nucleotides in a localized region vary from individual to individual, insertions and deletions which can vary in size from one nucleotides to millions of bases, and microsatellite or nucleotide repeats which vary by numbers of repeats. Nucleotide repeats include homogeneous repeats such as dinucleotide, trinucleotide, tetranucleotide or larger repeats, where the same sequence in repeated multiple times, and also heteronucleotide repeats where sequence motifs are found to repeat. For a given locus the number of nucleotide repeats can vary depending on the individual.

A polymorphic marker or site is the locus at which divergence occurs. Such a site can be as small as one base pair (an SNP). Polymorphic markers include, but are not limited to, restriction fragment length polymorphisms (RFLPs), variable number of tandem repeats (VNTR's), hypervariable regions, minisatellites, dinucleotide repeats, trinucleotide repeats, tetranucleotide repeats and other repeating patterns, simple sequence repeats and insertional elements, such as Alu. Polymorphic forms also are manifested as different Mendelian alleles for a gene. Polymorphisms can be observed by differences in proteins, protein modifications, RNA expression modification, DNA and RNA methylation, regulatory factors that alter gene expression and DNA replication, and any other manifestation of alterations in genomic nucleic acid or organelle nucleic acids.

Furthermore, numerous genes have polymorphic regions. Since individuals have any one of several allelic variants of a polymorphic region, individuals can be identified based on the type of allelic variants of polymorphic regions of genes. This can be used, for example, for forensic purposes. In other situations, it is crucial to know the identity of allelic variants that an individual has. For example, allelic differences in certain genes, for example, major histocompatibility complex (MHC) genes, are involved in graft rejection or graft versus host disease in bone marrow transplantation. Accordingly, it is highly desirable to develop rapid, sensitive, and accurate methods for determining the identity of allelic variants of polymorphic regions of genes or genetic lesions. Method or kit embodiments, as provided herein, can be used to genotype a subject by determining the identity of one or more allelic variants of one or more polymorphic regions in one or more genes or chromosomes of the subject. Genotyping a subject using a method as provided herein can be used for forensic or identity testing purposes and the polymorphic regions can be present in mitochondrial genes or can be short tandem repeats.

Single nucleotide polymorphisms (SNPs) are generally biallelic systems, that is, there are two alleles that an individual can have for any particular marker. This means that the information content per SNP marker is relatively low when compared to microsatellite markers, which can have upwards of 10 alleles. SNPs also tend to be very population-specific; a marker that is polymorphic in one population sometimes is not very polymorphic in another. SNPs, found approximately every kilobase (see Wang et al. (1998) Science 280:1077-1082), offer the potential for generating very high density genetic maps, which will be extremely useful for developing haplotyping systems for genes or regions of interest, and because of the nature of SNPS, they can in fact be the polymorphisms associated with the disease phenotypes under study. The low mutation rate of SNPs also makes them excellent markers for studying complex genetic traits.

Much of the focus of genomics has been on the identification of SNPs, which are important for a variety of reasons. SNP's allow indirect testing (association of haplotypes) and direct testing (functional variants). SNP's are the most abundant and stable genetic markers. Common diseases are best explained by common genetic alterations, and the natural variation in the human population aids in understanding disease, therapy and environmental interactions.

Thus, provided herein is a method for detecting a sequence variation in sample nucleic acid, which comprises (a) providing a nucleic acid from a sample; (b) preparing a mixture of the sample nucleic acid with a solid support described herein having solid phase nucleic acid under conditions in which a single molecule of sample nucleic acid hybridizes to a solid support molecule; (c) contacting the mixture with extension agents under conditions in which solid phase nucleic acid hybridized to sample nucleic acid is extended; (d) amplifying extended solid phase nucleic acid; (e) analyzing the sequence of the amplified nucleic acid of (d); and (f) based on a sequence determined in (e), identifying the presence or absence of the disease marker nucleotide sequence in the sample nucleic acid. The sample may be processed before step (b), by purifying the nucleic acid in the sample and/or fragmenting the sample nucleic acid, for example. Part (d) is optional in certain embodiments: the extended solid phase nucleic acid of (c) may be analyzed by sequencing (e), without amplification (d), using sequencing by synthesis methods described above, for example.

3. Detecting the Presence of Microbial Nucleic Acid Sequences Indicative of an Infection Processes and solid supports described herein can be used to determine the presence of microbial nucleic acid sequences indicative of an infection by identifying sequence variations that are present in the viral or bacterial nucleic acid sequences relative to one or more reference sequences. The reference sequence(s) can include, but are not limited to, sequences obtained from related non-infectious organisms, or sequences from host organisms.

Viruses, bacteria, fungi and other infectious organisms contain distinct nucleic acid sequences, including sequence variants, which are different from the sequences contained in the host cell, and in some instances different from the sequences of related species, subspecies, serotypes, and the like, which may form part of the normal flora or fauna of the host. A target DNA sequence can be part of a foreign genetic sequence such as the genome of an invading microorganism, including, for example, bacteria and their phages, viruses, fungi, protozoa, and the like. The processes provided herein are particularly applicable for distinguishing between different variants or strains of a microorganism (e.g., pathogenic, less pathogenic, resistant versus non-resistant and the like) in order, for example, to choose an appropriate therapeutic intervention. Examples of disease-causing viruses that infect humans and animals and that can be detected by a disclosed process include but are not limited to Retroviridae (e.g., human immunodeficiency viruses such as HIV-1 (also referred to as HTLV-III, LAV or HTLV-III/LAV; Ratner et al., Nature, 313:227-284 (1985); Wain Hobson et al., Cell, 40:9-17 (1985), HIV-2 (Guyader et al., Nature, 328:662-669 (1987); European Patent Publication No. 0 269 520; Chakrabarti et al., Nature, 328:543-547 (1987); European Patent Application No. 0 655 501, and other isolates such as HIV-LP (International Publication No. WO 94/00562); *Picornaviridae* (e.g., polioviruses, hepatitis A virus, (Gust et al., Intervirology, 20:1-7 (1983)); enteroviruses, human coxsackie viruses, rhinoviruses, echoviruses); *Calcivirdae* (e.g. strains that cause gastroenteritis); *Togaviridae* (e.g., equine encephalitis viruses, rubella viruses); *Flaviridae* (e.g., dengue viruses, encephalitis viruses, yellow fever viruses); *Coronaviridae* (e.g., coronaviruses); *Rhabdoviridae* (e.g., vesicular stomatitis viruses, rabies viruses); *Filoviridae* (e.g., ebola viruses); *Paramyxoviridae* (e.g., parainfluenza viruses, mumps virus, measles virus, respiratory syncytial virus); *Orthomyxoviridae* (e.g., influenza viruses); *Bungaviridae* (e.g., Hantaan viruses, bunga viruses, phleboviruses and Nairo viruses); *Arenaviridae* (hemorrhagic fever viruses); *Reoviridae* (e.g., reoviruses, orbiviruses and rotaviruses); *Birnaviridae; Hepadnaviridae* (Hepatitis B virus); *Parvoviridae* (parvoviruses); *Papovaviridae; Hepadnaviridae* (Hepatitis B virus); *Parvoviridae* (most adenoviruses); *Papovaviridae* (papilloma viruses, polyoma viruses); *Adenoviridae* (most adenoviruses); *Herpesviridae* (herpes simplex virus type 1 (HSV-1) and HSV-2, varicella zoster virus, cytomegalovirus, herpes viruses; *Poxviridae* (variola viruses, vaccinia viruses, pox viruses); *Iridoviridae* (e.g., African swine fever virus); and unclassified viruses (e.g., the etiological agents of Spongiform encephalopathies, the agent of delta hepatitis (thought to be a defective satellite of hepatitis B virus), the agents of non-A, non-B hepatitis (class 1=internally transmitted; class 2=parenterally transmitted, e.g., Hepatitis C); Norwalk and related viruses, and astroviruses.

Examples of infectious bacteria include but are not limited to *Helicobacter pyloris, Borelia burgdorferi, Legionella pneumophilia, Mycobacteria* sp. (e.g. *M. tuberculosis, M. avium, M. intracellulare, M. kansaii, M. gordonae), Salmonella, Staphylococcus aureus, Neisseria gonorrheae, Neisseria meningitidis, Listeria monocytogenes, Streptococcus pyogenes* (Group A *Streptococcus*), *Streptococcus agalactiae* (Group B *Streptococcus*), *Streptococcus* sp. (viridans group), *Streptococcus faecalis, Streptococcus bovis, Streptococcus* sp. (anaerobic species), *Streptococcus pneumoniae*, pathogenic *Campylobacter* sp., *Enterococcus* sp., *Haemophilus influenzae, Bacillus antracis, Corynebacterium diphtheriae, Corynebacterium* sp., *Erysipelothrix rhusiopathiae, Clostridium perfringens, Clostridium tetani, Escherichia coli, Enterobacter aerogenes, Klebsiella pneumoniae, Pasturella multocida, Bacteroides* sp., *Fusobacterium nucleatum, Streptobacillus moniliformis, Treponema pallidium, Treponema pertenue, Leptospira*, and *Actinomyces israelli*.

Examples of infectious fungi include but are not limited to *Cryptococcus neoformans, Histoplasma capsulatum, Coccidioides immitis, Blastomyces dermatitidis, Chlamydia trachomatis, Candida albicans*. Other infectious organisms include protists such as *Plasmodium falciparum* and *Toxoplasma gondii*.

Thus, provided herein is a method for detecting an infectious microbial nucleotide sequence in a sample, which comprises (a) providing a sample nucleic acid (e.g., taken from a subject); (b) preparing a mixture of the sample nucleic acid with a solid support described herein having solid phase nucleic acid under conditions in which a single molecule of the sample nucleic acid hybridizes to a solid support molecule; (c) contacting the mixture with extension agents under conditions in which solid phase nucleic acid hybridized to sample nucleic acid is extended; (d) amplifying extended solid phase nucleic acid; (e) analyzing the sequence of the amplified nucleic acid of (d); and (f) based on a sequence determined by part (e), identifying the presence or absence of the infectious microbial nucleotide sequence in the sample nucleic acid. The microbial nucleotide sequence may be compared to a reference microbial sequence in certain embodiments, and may be used, sometimes in conjunction with other information, to diagnose an infection of the subject. In some embodiments the sample may be processed before step (b), by purifying the nucleic acid in the sample and/or fragmenting the sample nucleic acid, for example. Part (d) is optional in certain embodiments: the extended solid phase nucleic acid of (c) may be analyzed by sequencing (e), without amplification (d), using sequencing by synthesis methods described above.

4. Detecting the Presence of Specific Viral Nucleic Acid Sequences in a Viral Mixture or Mixed Viral Population Processes and solid supports described herein can be used to determine the presence of specific viral nucleic acid sequences in a mixture of viral sequences or mixed population of viral sequences (e.g., for example a "homogenous" mixture containing only virus from the same genus, or "heterogeneous" populations as might be found in a sample taken from an environmental source or an immuno-deficient organism).

Recent evidence suggests that "viral mixtures" (e.g., mixed populations of virus from either the same or different genus and species, subspecies, cultivar and the like, hepatitis A, B, and C, for example), may lead to increased occurrence of certain diseases, cancer for example. This is particularly evident with hepatitis B virus (HBV) infection. An increase in the severity of the course of the disease and an increase in the reoccurrence of Hepatocellular carcinoma were seen in individuals co-infected with two or three subgenotypes of HBV, particularly subgenotypes C2 and B2 (Yin et al., "Role of hepatitis B virus genotype mixture, subgenotypes C2 and B2 on hepatocellular carcinoma: compared with chronic hepatitis B and asymptomatic carrier state in the same area" Carcinogenesis, 29(9): 1685-1691, 2008). The genetic variability of RNA viruses is also known in certain instances. This genetic variability, for example as seen in the Human Immunodeficiency Virus (HIV), has led to the discovery of "quasi-species" or mixed viral populations, with an increase in drug resistant forms of HIV discovered as a result of recombination between different HIV genotypes, due to anti-retroviral selective pressures.

Mixed viral populations are naturally occurring. It is estimated that oceans of the world contain greater than 22 metric tons of phage and virus particles (e.g., greater than $10^{31}$ particles, Rohwer and Edwards, "The phage proteomic tree: a genome based taxonomy for phage", Journal of Bacteriology, 184:4529-4535, 2002), some of which are known to be human pathogens (Griffin et al., Pathogenic human viruses in coastal waters. Clinical Microbiol. Rev. 16:129-143, 2003). Oceans of the world may have an average viral content in the lower range of the viral loads reported for human plasma from viremic patients. Even assuming minimal mutation and recombination rates, the equivalent of hundreds or thousands of complete "human genomes" worth of new genetic sequences are created daily. Early identification of potentially new pathogenic sequences using methods described herein to detect specific viral sequences in viral mixtures or mixed viral populations, may prove crucial to developing new and effective treatments. Further, viral populations are present in human populations and environmental samples, and can be assessed by processes and compositions described herein.

Processes provided herein are particularly applicable for distinguishing between different variants or strains, genotype, or subgenotypes of viruses (e.g., pathogenic, less pathogenic, resistant versus non-resistant and the like) in order, for example, to choose an appropriate therapeutic intervention. Examples of disease-causing viruses that infect humans and animals and that can be detected by a disclosed process include but are not limited to Retroviridae (e.g., human immunodeficiency viruses such as HIV-1 (also referred to as HTLV-III, LAV or HTLV-III/LAV; Ratner et al., Nature, 313:227-284 (1985); Wain Hobson et al., Cell, 40:9-17 (1985), HIV-2 (Guyader et al., Nature, 328:662-669 (1987); European Patent Publication No. 0 269 520; Chakrabarti et al., Nature, 328:543-547 (1987); European Patent Application No. 0 655 501), and other isolates such as HIV-LP (International Publication No. WO 94/00562); *Picornaviridae* (e.g., polioviruses, hepatitis A virus, (Gust et al., Intervirology, 20:1-7 (1983)); enteroviruses, human coxsackie viruses, rhinoviruses, echoviruses); *Calciviridae* (e.g. strains that cause gastroenteritis); Togaviridae (e.g., equine encephalitis viruses, rubella viruses); *Flaviridae* (e.g., dengue viruses, encephalitis viruses, yellow fever viruses); *Coronaviridae* (e.g., coronaviruses); *Rhabdoviridae* (e.g., vesicular stomatitis viruses, rabies viruses); *Filoviridae* (e.g., ebola viruses); *Paramyxoviridae* (e.g., parainfluenza viruses, mumps virus, measles virus, respiratory syncytial virus); *Orthomyxoviridae* (e.g., influenza viruses); *Bungaviridae* (e.g., Hantaan viruses, bunga viruses, phleboviruses and Nairo viruses); *Arenaviridae* (hemorrhagic fever viruses); *Reoviridae* (e.g., reoviruses, orbiviruses and rotaviruses); *Birnaviridae*; *Hepadnaviridae* (Hepatitis B virus); *Parvoviridae* (parvoviruses); *Papovaviridae*; *Hepadnaviridae* (Hepatitis B virus); *Parvoviridae* (most adenoviruses); *Papovaviridae* (papilloma viruses, polyoma viruses); *Adenoviridae* (most adenoviruses); *Herpesviridae* (herpes simplex virus type 1 (HSV-1) and HSV-2, varicella zoster virus, cytomegalovirus, herpes viruses; *Poxviridae* (variola viruses, vaccinia viruses, pox viruses); *Iridoviridae* (e.g., African swine fever virus); and unclassified viruses (e.g., the etiological agents of Spongiform encephalopathies, the agent of delta hepatitis (thought to be a defective satellite of hepatitis B virus), the agents of non-A, non-B hepatitis (class 1=internally transmitted; class 2=parenterally transmitted, e.g., Hepatitis C); Norwalk and related viruses, and astroviruses. In certain embodiments the processes provided herein may be used to detect hepatitis B nucleic acid sequences in a mixture of Hepadnaviridae sequences.

Thus, provided herein is a method for detecting specific viral nucleotide sequences in a viral mixture or mixed viral population sample, which comprises (a) providing a sample nucleic acid (e.g., taken from a subject or ocean); (b) preparing a mixture of the sample nucleic acid with a solid support described herein having solid phase nucleic acid under conditions in which a single molecule of the sample nucleic acid hybridizes to a solid support molecule; (c) contacting the mixture with extension agents under conditions in which solid phase nucleic acid hybridized to sample nucleic acid is extended; (d) amplifying extended solid phase nucleic acid; (e) analyzing the sequence of the amplified nucleic acid of (d); and (f) based on a sequence determined by part (e), identifying the presence or absence of the viral nucleotide sequence in the sample nucleic acid. The viral nucleotide sequence may be compared to a reference viral sequence in certain embodiments, and may be used, sometimes in conjunction with other information, to detect the presence of a specific viral nucleic acid sequence, or for example to diagnose an infection of a subject. In some embodiments the sample may be processed before step (b), by purifying the nucleic acid in the sample and/or fragmenting the sample nucleic acid, for example. Part (d) is optional in certain embodiments: the extended solid phase nucleic acid of (c) may be analyzed by sequencing (e), without amplification (d), using sequencing by synthesis methods described above.

5. Antibiotic Profiling

Processes and solid supports described herein can be utilized to identify nucleotide changes involved in drug resistance, including antibiotic resistance. Genetic loci involved in resistance to isoniazid, rifampin, streptomycin, fluoroquinolones, and ethionamide have been identified [Heym et al., Lancet 344:293 (1994) and Morris et al., J. Infect. Dis. 171:954 (1995)]. A combination of isoniazid (inh) and rifampin (rif) along with pyrazinamide and ethambutol or streptomycin, is routinely used as the first line of attack against confirmed cases of *M. tuberculosis* [Banerjee et al., Science 263:227 (1994)]. The increasing incidence of such resistant strains necessitates the development of rapid assays to detect them and thereby reduce the expense and community health hazards of pursuing ineffective, and possibly detrimental, treatments. The identification of some of the genetic loci involved in drug resistance has facilitated the adoption of mutation detection technologies for rapid screening of nucleotide changes that result in drug resistance. In addition, the technology facilitates treatment monitoring and tracking or microbial population structures.

Thus, in some embodiments the target nucleotide sequence identified may be (i) a genetic locus mutated as a result of an organism (e.g., the sequence will be present if a drug-resistant organism is present); (ii) a genetic locus that does not change as a result of drug resistance (e.g., such a sequence from a pathogen will diminish over time if the drug depletes the organism); (iii) a nucleotide sequence from a particular strain not resistant to the drug. Accordingly, provided herein is a method for determining the presence of drug resistance, which comprises (a) providing a nucleic acid from a sample; (b) preparing a mixture of the sample nucleic acid with a solid support described herein having solid phase nucleic acid under conditions in which a single molecule of the sample nucleic acid hybridizes to a solid support molecule; (c) contacting the mixture with extension agents under conditions in which solid phase nucleic acid hybridized to sample nucleic acid is extended; (d) amplifying extended solid phase nucleic acid; (e) analyzing the sequence of the amplified nucleic acid of (d); and (f) based on a sequence determined in (e), detecting the presence or absence of a target nucleic acid sequence indicative of drug resistance. The presence of a sequence indicative of resistance to a first drug may be identified, and an alternative drug may be prescribed. In some embodiments the sample may be processed before step (b), by purifying the nucleic acid in the sample and/or fragmenting the sample nucleic acid, for example. Part (d) is optional in certain embodiments: the extended solid phase nucleic acid of (c) may be analyzed by sequencing (e), without amplification (d), using sequencing by synthesis methods described above.

6. Identifying Disease Markers

Processes and solid supports described herein can be utilized to rapidly and accurately identify sequence variations that are genetic markers of disease, which can be used to diagnose or determine the prognosis of a disease. Diseases characterized by genetic markers can include, but are not limited to, atherosclerosis, obesity, diabetes, autoimmune disorders, and cancer. Diseases in all organisms have a genetic component, whether inherited or resulting from the body's response to environmental stresses, such as viruses and toxins. The ultimate goal of ongoing genomic research is to use this information to develop new ways to identify, treat and potentially cure these diseases. The first step has been to screen disease tissue and identify genomic changes at the level of individual samples. The identification of these "disease" markers is dependent on the ability to detect changes in genomic markers in order to identify errant genes or sequence variants. Genomic markers (all genetic loci including single nucleotide polymorphisms (SNPs), microsatellites and other noncoding genomic regions, tandem repeats, introns and exons) can be used for the identification of all organisms, including humans. These markers provide a way to not only identify populations but also allow stratification of populations according to their response to disease, drug treatment, resistance to environmental agents, and other factors.

Thus, provided herein is a method for detecting a disease marker nucleotide sequence, which comprises (a) providing a nucleic acid from a sample; (b) preparing a mixture of the sample nucleic acid with a solid support described herein having solid phase nucleic acid under conditions in which a single molecule of the sample nucleic acid hybridizes to a solid support molecule; (c) contacting the mixture with extension agents under conditions in which solid phase nucleic acid hybridized to sample nucleic acid is extended; (d) amplifying extended solid phase nucleic acid; (e) analyzing the sequence of the amplified nucleic acid of (d); and (f) based on a sequence determined by part (e), identifying the presence or absence of the disease marker nucleotide sequence in the sample nucleic acid. In some embodiments the sample may be processed before step (b), by purifying the nucleic acid in the sample and/or fragmenting the sample nucleic acid, for example. Part (d) is optional in certain embodiments: the extended solid phase nucleic acid of (c) may be analyzed by sequencing (e), without amplification (d), using sequencing by synthesis methods described above.

7. Haplotyping

Processes and solid supports described herein can be used to detect haplotypes. In any diploid cell, there are two haplotypes at any gene or other chromosomal segment that contain at least one distinguishing variance. In many well-studied genetic systems, haplotypes are more powerfully correlated with phenotypes than single nucleotide variations. Thus, the determination of haplotypes is valuable for understanding the genetic basis of a variety of phenotypes including disease predisposition or susceptibility, response to therapeutic interventions, and other phenotypes of interest in medicine, animal husbandry, and agriculture.

Haplotyping procedures as provided herein permit the selection of a portion of sequence from one of an individual's two homologous chromosomes and to genotype linked SNPs on that portion of sequence. The direct resolution of haplotypes can yield increased information content, improving the diagnosis of any linked disease genes or identifying linkages associated with those diseases.

Thus, provided herein is a method for identifying a haplotypes comprising two or more nucleotides, which comprises (a) providing a nucleic acid from a sample, wherein the nucleic acid is from one chromosome of a diploid organism; (b) preparing a mixture of the sample nucleic acid with a solid support described herein having solid phase nucleic acid under conditions in which a single molecule of the sample nucleic acid hybridizes to a solid support molecule; (c) contacting the mixture with extension agents under conditions in which solid phase nucleic acid hybridized to sample nucleic acid is extended; (d) amplifying extended solid phase nucleic acid; (e) analyzing the sequence of the amplified nucleic acid of (d); and (f) based on a sequence determined by part (e), determining the haplotype in the sample nucleic acid. In some embodiments the sample may be processed before step (b), by purifying the nucleic acid in the sample and/or fragmenting the sample nucleic acid, for example. Part (d) is optional in certain embodiments: the extended solid phase nucleic acid of (c) may be analyzed by sequencing (e), without amplification (d), using sequencing by synthesis methods described above.

8. Microsatellites

Processes and solid supports described herein allow for rapid, unambiguous detection of sequence variations that are microsatellites. Microsatellites (sometimes referred to as variable number of tandem repeats or VNTRs) are short tandemly repeated nucleotide units of one to seven or more bases, the most prominent among them being di-, tri-, and tetranucleotide repeats. Microsatellites are present every 100,000 by in genomic DNA (J. L. Weber and P. E. Can, Am. J. Hum. Genet. 44, 388 (1989); J. Weissenbach et al., Nature 359, 794 (1992)). CA dinucleotide repeats, for example, make up about 0.5% of the human extra-mitochondrial genome; CT and AG repeats together make up about 0.2%. CG repeats are rare, most probably due to the regulatory function of CpG islands. Microsatellites are highly polymorphic with respect to length and widely distributed over the whole genome with a main abundance in non-coding sequences, and their function within the genome is unknown.

Microsatellites are important in forensic applications, as a population will maintain a variety of microsatellites characteristic for that population and distinct from other populations, which do not interbreed. Many changes within microsatellites can be silent, but some can lead to significant alterations in gene products or expression levels. For example, trinucleotide repeats found in the coding regions of genes are affected in some tumors (C. T. Caskey et al., Science 256, 784 (1992) and alteration of the microsatellites can result in a genetic instability that results in a predisposition to cancer (P. J. McKinnen, Hum. Genet. 1 75, 197 (1987); J. German et al., Clin. Genet. 35, 57 (1989)).

Thus, provided herein is a method for detecting a microsatellite sequence, which comprises (a) providing a nucleic acid from a sample; (b) preparing a mixture of the sample nucleic acid with a solid support described herein having solid phase nucleic acid under conditions in which a single molecule of the sample nucleic acid hybridizes to a solid support molecule; (c) contacting the mixture with extension agents under conditions in which solid phase nucleic acid hybridized to sample nucleic acid is extended; (d) amplifying extended solid phase nucleic acid; (e) analyzing the sequence of the amplified nucleic acid of (e); and (f) based on a sequence determined by part (d), determining whether the microsatellite sequence is present in the sample nucleic acid. A microsatellite sequence may be a full microsatellite sequence or a portion of a full microsatellite sequence. In some embodiments the sample may be processed before step (b), by purifying the nucleic acid in the sample and/or fragmenting the sample nucleic acid, for example. Part (d) is optional in certain embodiments: the extended solid phase nucleic acid of (c) may be analyzed by sequencing (e), without amplification (d), using sequencing by synthesis methods described above.

9. Short Tandem Repeats

Processes and solid supports described herein can be used to identify short tandem repeat (STR) regions in some target sequences of the human genome relative to, for example, reference sequences in the human genome that do not contain STR regions. STR regions are polymorphic regions that are not related to any disease or condition. Many loci in the human genome contain a polymorphic short tandem repeat (STR) region. STR loci contain short, repetitive sequence elements of 3 to 7 base pairs in length. It is estimated that there are 200,000 expected trimeric and tetrameric STRs, which are present as frequently as once every 15 kb in the human genome (see, e.g., International PCT application No. WO 9213969 A1, Edwards et al., Nucl. Acids Res. 19:4791 (1991); Beckmann et al. (1992) Genomics 12:627-631). Nearly half of these STR loci are polymorphic, providing a rich source of genetic markers. Variation in the number of repeat units at a particular locus is responsible for the observed sequence variations reminiscent of variable nucleotide tandem repeat (VNTR) loci (Nakamura et al. (1987) Science 235:1616-1622); and minisatellite loci (Jeffreys et al. (1985) Nature 314:67-73), which contain longer repeat units, and microsatellite or dinucleotide repeat loci (Luty et al. (1991) Nucleic Acids Res. 19:4308; Litt et al. (1990) Nucleic Acids Res. 18:4301; Litt et al. (1990) Nucleic Acids Res. 18:5921; Luty et al. (1990) Am. J. Hum. Genet. 46:776-783; Tautz (1989) Nucl. Acids Res. 17:6463-6471; Weber et al. (1989) Am. J. Hum. Genet. 44:388-396; Beckmann et al. (1992) Genomics 12:627-631).

Examples of STR loci include, but are not limited to, pentanucleotide repeats in the human CD4 locus (Edwards et al., Nucl. Acids Res. 19:4791 (1991)); tetranucleotide repeats in the human aromatase cytochrome P-450 gene (CYP19; Polymeropoulos et al., Nucl. Acids Res. 19:195 (1991)); tetranucleotide repeats in the human coagulation factor XIII A subunit gene (F13A1; Polymeropoulos et al., Nucl. Acids Res. 19:4306 (1991)); tetranucleotide repeats in the F13B locus (Nishimura et al., Nucl. Acids Res. 20:1167 (1992)); tetranucleotide repeats in the human c-les/fps, proto-oncogene (FES; Polymeropoulos et al., Nucl. Acids Res. 19:4018 (1991)); tetranucleotide repeats in the LFL gene (Zuliani et al., Nucl. Acids Res. 18:4958 (1990)); trinucleotide repeat sequence variations at the human pancreatic phospholipase A-2 gene (PLA2; Polymeropoulos et al., Nucl. Acids Res. 18:7468 (1990)); tetranucleotide repeat sequence variations in the VWF gene (Ploos et al., Nucl. Acids Res. 18:4957 (1990)); and tetranucleotide repeats in the human thyroid peroxidase (hTPO) locus (Anker et al., Hum. Mol. Genet. 1:137 (1992)).

Thus, provided herein is a method for detecting a short tandem repeat sequence, which comprises (a) providing a nucleic acid from a sample; (b) preparing a mixture of the sample nucleic acid with a solid support described herein having solid phase nucleic acid under conditions in which a single molecule of the sample nucleic acid hybridizes to a solid support molecule; (c) contacting the mixture with extension agents under conditions in which solid phase nucleic acid hybridized to sample nucleic acid is extended; (d) amplifying extended solid phase nucleic acid; (e) analyzing the sequence of the amplified nucleic acid of (d); and (f) based on a sequence determined in (e), determining whether the short tandem repeat sequence is present in the sample nucleic acid. A short tandem repeat sequence may be a full STR sequence or a portion of a full STR sequence. In some embodiments the sample may be processed before step (b), by purifying the nucleic acid in the sample and/or fragmenting the sample nucleic acid, for example. Part (d) is optional in certain embodiments: the extended solid phase nucleic acid of (c) may be analyzed by sequencing (e), without amplification (d), using sequencing by synthesis methods described above.

10. Organism Identification

Processes and solid supports described herein can be utilized to identify polymorphic STR loci and other polymorphic regions useful for discriminating one organism from another. Certain polymorphic STR loci and other polymorphic regions of genes are sequence variations that are useful markers for human identification, paternity and maternity testing, genetic mapping, immigration and inheritance disputes, zygosity testing in twins, tests for inbreeding in humans, quality control of human cultured cells, identification of human remains, and testing of semen samples, blood stains, microbes and other material in forensic medicine. Such loci also are useful markers in commercial animal breeding and pedigree analysis and in commercial plant breeding. Traits of economic importance in plant crops and animals can be identified through linkage analysis using polymorphic DNA markers. Efficient and accurate methods for determining the identity of such loci are provided herein.

Thus, provided herein is a method for detecting a target nucleotide sequence of one organism, which comprises (a) providing a nucleic acid from a sample; (b) preparing a mixture of the sample nucleic acid with a solid support described herein having solid phase nucleic acid under conditions in which a single molecule of the sample nucleic acid hybridizes to a solid support molecule; (c) contacting the mixture with extension agents under conditions in which solid phase nucleic acid hybridized to sample nucleic acid is extended; (d) amplifying extended solid phase nucleic acid; (e) analyzing the sequence of the amplified nucleic acid of (d); and (f) based on a sequence determined in (e), determining whether the target nucleotide sequence is present. If the presence of a first organism that resides in a second organism is being detected, a target nucleotide sequence present in nucleic acid from the first organism that is not present in nucleic acid of the second organism generally is selected (e.g., a nucleotide sequence in a pathogen nucleic acid that is not present in a human nucleic acid; a nucleotide sequence in a fetus nucleic acid that is not present in a maternal nucleic acid). In some embodiments the sample may be processed before step (b), by purifying the nucleic acid in the sample and/or fragmenting the sample nucleic acid, for example. Part (d) is optional in certain embodiments: the extended solid phase nucleic acid of (c) may be analyzed by sequencing (e), without amplification (d), using sequencing by synthesis methods described above.

11. Detecting Allelic Variation

Processes and solid supports described herein allow for high-throughput, fast and accurate detection of allelic variants. Human populations are heterogeneous in terms of susceptibility to particular diseases or responses to therapeutic interventions. Increasing evidence suggests that allelic variation in gene expression is a widespread phenomenon, and may contribute to phenotypic variation between individuals. As more genomes are sequenced, the identification and characterization of the causes of heritable variation within a species will be increasingly important. Allelic variation can occur be observed between ethnic or regional populations, and within ethnic and regional populations. In some instances intra-population variation can be found within relatively small populations. Heritable allelic variation in gene expression may contribute to sporadic and familial disease, but is relatively unexplored. Understanding allelic variation may help provide insight into a number of genetic heterogeneity phenomena, including but not limited to genetic imprinting, disease susceptibility and therapeutic response.

Studies of allelic variation involve not only detection of a specific sequence in a complex background, but also the discrimination between sequences with few, or single, nucleotide differences. Allelic variations studies can be performed on DNA or RNA, thus correlations can be made between allelic variants, SNP's and expression levels. One method for detecting the degree of variation in allelic expression at any specific locus is to quantitatively genotype mRNA from individuals heterozygous for an exonic single nucleotide polymorphism (SNP) in the gene of interest. If there is no allelic variation in gene expression then the two alleles of the SNP should be expressed at the same level, but where there is allelic differential expression one allele will be found at a higher level than the other.

Thus, provided herein is a method for detecting a sequence variation in a target nucleotide sequence, which comprises (a) providing a nucleic acid from a sample; (b) preparing a mixture of the sample nucleic acid with a solid support described herein having solid phase nucleic acid under conditions in which a single molecule of the sample nucleic acid hybridizes to a solid support molecule; (c) contacting the mixture with extension agents under conditions in which solid phase nucleic acid hybridized to sample nucleic acid is extended; (d) amplifying extended solid phase nucleic acid; (e) analyzing the sequence of the amplified nucleic acid of (d); and (f) based on a sequence determined in (e), determining whether a sequence variation in the target nucleotide sequence is present. In some embodiments the sample may be processed before step (b), by purifying the nucleic acid in the sample and/or fragmenting the sample nucleic acid, for example. Part (d) is optional in certain embodiments: the extended solid phase nucleic acid of (c) may be analyzed by sequencing (e), without amplification (d), using sequencing by synthesis methods described above.

12. Determining Allelic Frequency

Processes and solid supports described herein are useful for identifying one or more genetic markers whose frequency changes within the population as a function of age, ethnic group, sex or some other criteria. For example, the age-dependent distribution of ApoE genotypes is known in the art (see, Schechter et al. (1994) Nature Genetics 6:29-32). The frequencies of sequence variations known to be associated at some level with disease can also be used to detect or monitor progression of a disease state. For example, the N291 S polymorphism (N291 S) of the Lipoprotein Lipase gene, which results in a substitution of a serine for an asparagine at amino acid codon 291, leads to reduced levels of high density lipoprotein cholesterol (HDL-C) that is associated with an increased risk of males for arteriosclerosis and in particular myocardial infarction (see, Reymer et al. (1995) Nature Genetics 10:28-34). In addition, determining changes in allelic frequency can allow the identification of previously unknown sequence variations and ultimately a gene or pathway involved in the onset and progression of disease.

Thus, provided herein is a method for determining the frequency of a target nucleotide sequence in a population of individuals, which comprises (a) providing a sample nucleic acid (e.g., taken from a subject); (b) preparing a mixture of the sample nucleic acid with a solid support described herein having solid phase nucleic acid under conditions in which a single molecule of the sample nucleic acid hybridizes to a solid support molecule; (c) contacting the mixture with extension agents under conditions in which solid phase nucleic acid hybridized to sample nucleic acid is extended; (d) amplifying the extended nucleic acid; (e) analyzing the sequence of the amplified nucleic acid; (f) identifying the presence or absence of the target nucleotide sequence according in (e); and (g) repeating steps (a) to (f) for other individuals of the population and determining the frequency of the target nucleotide sequence in the population. In some embodiments the sample may be processed before step (b), by purifying the nucleic acid in the sample and/or fragmenting the sample nucleic acid, for example. In some embodiments methylated nucleotides in the sample nucleic acid may be converted to another nucleotide using methods known in the art, such as bisulfite conversion of methylated cytosine to uracil, for example. Part (d) is optional in certain embodiments: the extended solid phase nucleic acid of (c) may be analyzed by sequencing (e), without amplification (d), using sequencing by synthesis methods described above.

13. Epigenetics

Processes and solid supports described herein can be used to study variations in a target nucleic acid or protein relative to a reference nucleic acid or protein that are not based on sequence, e.g., the identity of bases or amino acids that are the naturally occurring monomeric units of the nucleic acid or protein. For example, the specific cleavage reagents employed in the methods provided herein may recognize differences in sequence-independent features such as methylation patterns, the presence of modified bases or amino acids, or differences in higher order structure between the target molecule and the reference molecule, to generate fragments that are cleaved at sequence-independent sites. Epigenetics is the study of the inheritance of information based on differences in gene expression rather than differences in gene sequence. Epigenetic changes refer to mitotically and/or meiotically heritable changes in gene function or changes in higher order nucleic acid structure that cannot be explained by changes in nucleic acid sequence. Examples of features that are subject to epigenetic variation or change include, but are not limited to, DNA methylation patterns in animals, histone modification and the Polycomb-trithorax group (Pc-G/tx) protein complexes (see, e.g., Bird, A., Genes Dev., 16:6-21 (2002)).

Epigenetic changes usually, although not necessarily, lead to changes in gene expression that are usually, although not necessarily, inheritable. For example, as discussed further below, changes in methylation patterns sometimes may be an early event in cancer and other disease development and progression. In many cancers, certain genes are inappropriately switched off or switched on due to aberrant methylation. The ability of methylation patterns to repress or activate transcription can be inherited. The Pc-G/trx protein complexes, like methylation, can repress transcription in a heritable fashion. The Pc-G/trx multiprotein assembly is targeted to specific regions of the genome where it effectively freezes the embryonic gene expression status of a gene, whether the gene is active or inactive, and propagates that state stably through development. The ability of the Pc-G/trx group of proteins to target and bind to a genome affects only the level of expression of the genes contained in the genome, and not the properties of the gene products. The methods provided herein can be used with specific cleavage reagents that identify variations in a target sequence relative to a reference sequence that are based on sequence-independent changes, such as epigenetic changes.

Thus, provided herein is a method for the epigenetic analysis of a target nucleotide sequence, which comprises (a) providing a nucleic acid from a sample in which methylated nucleotides or non-methylated nucleotides have been converted to another nucleotide moiety; (b) preparing a mixture of the sample nucleic acid with a solid support described herein having solid phase nucleic acid under conditions in which a single molecule of the sample nucleic acid hybridizes to a solid support molecule; (c) contacting the mixture with extension agents under conditions in which solid phase nucleic acid hybridized to sample nucleic acid; (d) preparing an emulsion; (e) amplifying the extended nucleic acid; (f) analyzing the sequence of the amplified nucleic acid; and (g) based on a sequence determined in (f), comparing the methylation pattern of the target nucleic acid to the methylation pattern of a reference nucleic acid. In some embodiments the sample may be processed before step (b), by purifying the nucleic acid in the sample and/or fragmenting the sample nucleic acid, for example. Part (d) is optional in certain embodiments: the extended solid phase nucleic acid of (c) may be analyzed by sequencing (f), without amplification (e), using sequencing by synthesis methods described above.

The term "another nucleotide moiety" as used herein refers to a nucleotide moiety other than the nucleotide that was methylated or non-methylated. The "another nucleotide moiety" may be naturally occurring or non-naturally occurring. Methylated nucleotides in the sample nucleic acid may be converted to another nucleotide moiety using methods known in the art, such as bisulfite conversion of methylated cytosine to uracil, for example.

14. Methylation Patterns

Processes and solid supports described herein can be used to detect sequence variations that are epigenetic changes in the target sequence, such as a change in methylation patterns in the target sequence. Analysis of cellular methylation is an emerging research discipline. The covalent addition of methyl groups to cytosine is primarily present at CpG dinucleotides (microsatellites). Although the function of CpG islands not located in promoter regions remains to be explored, CpG islands in promoter regions are of special interest because their methylation status regulates the transcription and expression of the associated gene. Methylation of promotor regions leads to silencing of gene expression. This silencing is permanent and continues through the process of mitosis. Due to its significant role in gene expression, DNA methylation has an impact on developmental processes, imprinting and X-chromosome inactivation as well as tumor genesis, aging, and also suppression of parasitic DNA. Methylation is thought to be involved in the cancerogenesis of many widespread tumors, such as lung, breast, and colon cancer, an in leukemia. There is also a relation between methylation and protein dysfunctions (long Q-T syndrome) or metabolic diseases (transient neonatal diabetes, type 2 diabetes).

Bisulfite treatment of genomic DNA can be utilized to analyze positions of methylated cytosine residues within the DNA. Treating nucleic acids with bisulfite deaminates cytosine residues to uracil residues, while methylated cytosine remains unmodified. Thus, by comparing the sequence of a target nucleic acid that is not treated with bisulfite with the sequence of the nucleic acid that is treated with bisulfite in the methods provided herein, the degree of methylation in a nucleic acid as well as the positions where cytosine is methylated can be deduced.

Methylation analysis via restriction endonuclease reaction is made possible by using restriction enzymes, which have methylation-specific recognition sites, such as HpaII and MSPI. The basic principle is that certain enzymes are blocked by methylated cytosine in the recognition sequence. Once this differentiation is accomplished, subsequent analysis of the resulting fragments can be performed using the methods as provided herein.

These methods can be used together in combined bisulfite restriction analysis (COBRA). Treatment with bisulfite causes a loss in BstUI recognition site in amplified PCR product, which causes a new detectable fragment to appear on analysis compared to untreated sample. The cleavage-based methods provided herein can be used in conjunction with specific cleavage of methylation sites to provide rapid, reliable information on the methylation patterns in a target nucleic acid sequence.

Thus, provided herein is a method for analyzing a methylation pattern of a target nucleotide sequence, which comprises (a) providing a nucleic acid from a sample in which methylated nucleotides or non-methylated nucleotides have been converted to another nucleotide moiety; (b) preparing a mixture of the sample nucleic acid with a solid support described herein having solid phase nucleic acid under conditions in which a single molecule of the sample nucleic acid hybridizes to a solid support molecule; (c) contacting the mixture with extension agents under conditions in which solid phase nucleic acid hybridized to sample nucleic acid is extended; (d) amplifying the extended nucleic acid; (e) analyzing the sequence of the amplified nucleic acid; and (f) determining the methylation pattern based on the sequence in (e). In some embodiments the sample may be processed before step (b), by purifying the nucleic acid in the sample and/or fragmenting the sample nucleic acid, for example. Part (d) is optional in certain embodiments: the extended solid phase nucleic acid of (c) may be analyzed by sequencing (e), without amplification (d), using sequencing by synthesis methods described above.

15. Resequencing

Processes and solid supports described herein are useful for rapid resequencing analyses. The dramatically growing amount of available genomic sequence information from various organisms increases the need for technologies allowing large-scale comparative sequence analysis to correlate sequence information to function, phenotype, or identity. The application of such technologies for comparative sequence analysis can be widespread, including SNP discovery and sequence-specific identification of pathogens. Therefore, resequencing and high-throughput mutation screening technologies are critical to the identification of mutations underlying disease, as well as the genetic variability underlying differential drug response.

Several approaches have been developed in order to satisfy these needs. A current technology for high-throughput DNA sequencing includes DNA sequencers using electrophoresis and laser-induced fluorescence detection. Electrophoresis-based sequencing methods have inherent limitations for detecting heterozygotes and are compromised by GC compressions. Thus a DNA sequencing platform that produces digital data without using electrophoresis will overcome these problems. Matrix-assisted laser desorption/ionization time-of-flight mass spectrometry (MALDI-TOF MS) measures DNA fragments with digital data output. The methods of specific cleavage fragmentation analysis provided herein allow for high-throughput, high speed and high accuracy in the detection of sequence variations relative to a reference sequence. This approach makes it possible to routinely use MALDI-TOF MS sequencing for accurate mutation detection, such as screening for founder mutations in BRCA1 and BRCA2, which are linked to the development of breast cancer.

Thus, the invention in part provides a method for resequencing a target nucleotide sequence, which comprises (a) providing a sample nucleic acid (e.g., taken from a subject); (b) preparing a mixture of the sample nucleic acid with a solid support described herein having solid phase nucleic acid under conditions in which a single molecule of the sample nucleic acid hybridizes to a solid support molecule; (c) contacting the mixture with extension agents under conditions in which solid phase nucleic acid hybridized to sample nucleic acid is extended; (d) amplifying the extended nucleic acid; (e) analyzing the sequence of the amplified nucleic acid; and (f) comparing a sequence determined in part (e) to a reference nucleotide sequence, whereby the target nucleotide sequence is resequenced. The reference sequence may be a nucleotide sequence already identified from the sample. In some embodiments the sample may be processed before step (b), by purifying the nucleic acid in the sample and/or fragmenting the sample nucleic acid, for example.

16. Multiplexing

Processes and solid supports described herein can allow for the high-throughput detection or discovery of sequences in a plurality of target sequences. Multiplexing refers to the simultaneous detection of more than one sequence, polymorphism or sequence variation. Multiplexing allows the simultaneous processing of many sequencing templates by pooling these at the earliest stages of the preparation procedure and resolves them into individual sequences at the latest possible stage of the sequencing process, thus enabling a high throughput of templates with a reduction in repetitious steps. Methods for performing multiplexed reactions, particularly in conjunction with mass spectrometry, are known (see, e.g., U.S. Pat. Nos. 6,043,031, 5,547,835 and International PCT application No. WO 97/37041).

Multiplexing can be performed, for example, for the same target nucleic acid sequence using different complementary specific cleavage reactions as provided herein, or for different target nucleic acid sequences, and the cleavage patterns can in turn be analyzed against a plurality of reference nucleic acid sequences. Several mutations or sequence variations can also be simultaneously detected on one target sequence by employing the methods provided herein where each sequence variation corresponds to a different cleavage product relative to the cleavage pattern of the reference nucleic acid sequence. Multiplexing provides the advantage that a plurality of sequence variations can be identified in as few as a single mass spectrum, as compared to having to perform a separate mass spectrometry analysis for each individual sequence variation. The methods provided herein lend themselves to high-throughput, highly-automated processes for analyzing sequence variations with high speed and accuracy, with the added advantage of identification of sequences not normally readable using gel electrophoresis based methods. In some embodiments multiplex sequence analysis can also be combined with other non-limiting methods commonly known in the art, such as DNA sequencing by exonuclease degradation, for example.

Thus, provided herein is a method for analyzing a target nucleotide sequence, which comprises (a) providing a nucleic acid from a sample; (b) preparing a mixture of the sample nucleic acid with a solid support described herein having solid phase nucleic acid under conditions in which a single molecule of the sample nucleic acid hybridizes to a solid support molecule; (c) contacting the mixture with extension agents under conditions in which solid phase nucleic acid hybridized to sample nucleic acid is extended; (d) amplifying the extended nucleic acid; (e) analyzing the sequence of the amplified nucleic acid; and (f) identifying two more sequences in the sample nucleic acid. In some embodiments the sample may be processed before step (b), by purifying the nucleic acid in the sample and/or fragmenting the sample nucleic acid, for example. Part (d) is optional in certain embodiments: the extended solid phase nucleic acid of (c) may be analyzed by sequencing (e), without amplification (d), using sequencing by synthesis methods described above.

17. Disease Outbreak Monitoring

Processes and solid supports described herein can be used to monitor disease outbreaks. In times of global transportation and travel outbreaks of pathogenic endemics require close monitoring to prevent their worldwide spread and enable control. DNA based typing by high-throughput technologies (e.g., using DNA chips, DNA array technologies, and the like) enable a rapid sample throughput in a comparatively short time, as required in an outbreak situation. Currently, traditional methods of disease outbreak monitoring may take as long as 7 to 10 days to identify pathogenic microorganisms. Using high-throughput technologies may offer significant time savings in the critical initial stages of disease outbreak monitoring, by reducing identification times from 7 to 10 days to less than 2 days. Monitoring is performed by detecting one or more microbial marker regions (e.g., SNP's, unique regions of rRNA and the like) in one or more samples. A genus, species, strain or subtype of a microorganism can be monitored, using molecular markers to identify the presence or absence of nucleic acid sequences specific to known pathogenic microorganisms.

Thus, provided herein is a method for monitoring a disease outbreak, which comprises (a) providing a nucleic acid from a sample; (b) preparing a mixture of the sample nucleic acid with a solid support described herein having solid phase nucleic acid under conditions in which a single molecule of the sample nucleic acid hybridizes to a solid support molecule; (c) contacting the mixture with extension agents under conditions in which solid phase nucleic acid hybridized to sample nucleic acid is extended; (d) amplifying extended solid phase nucleic acid; (e) analyzing the sequence of the amplified nucleic acid in (d); and (f) comparing a sequence determined in (e) to a reference sequence, whereby the disease outbreak is monitored. The sample may be processed before step (b), by purifying the nucleic acids and/or fragmenting the nucleic acids, for example. The disease outbreak may be monitored by determining whether (i) there are new sequences as determined in part (e) not present in a reference sample (e.g., indicating that new pathogens are present in a population as part of a disease outbreak) and (ii) there are fewer sequences as determined in part (e) than present in a reference sample (e.g., indicating certain pathogens no longer are a threat as part of the disease outbreak). A reference sequence may be from a sample taken from the same individual(s) at a different point in time (e.g., earlier point of time). In some embodiments the sample may be processed before step (b), by purifying the nucleic acid in the sample and/or fragmenting the sample nucleic acid, for example. Part (d) is optional in certain embodiments: the extended solid phase nucleic acid of (c) may be analyzed by sequencing (e), without amplification (d), using sequencing by synthesis methods described above. In some embodiments multiplexed comparative sequence analysis in conjunction with matrix-assisted laser desorption/ionization time-of-flight mass spectrometry (MALDI-TOF MS) analysis, can be used with embodiments described herein to monitor disease outbreaks.

18. Vaccine Quality Control and Production Clone Quality Control

Processes and solid supports described herein can be used to control the identity of recombinant production clones, which can be vaccines or e.g. insulin or any other production clone or biological or medical product. The entire sequence or one or more portions of a clone or vaccine can be analyzed in production samples and lots. Sequences determined by processes described herein can be compared to a reference sequence for the clone or vaccine to monitor quality control. Quality control monitoring of this type can allow detection of spontaneous mutations or genetic rearrangement at various stages of production in large scale bioreactors, thus allowing more efficient resource management by allowing early detection and shut down of processes which have been monitored and show deviation from the expected product Thus, provided herein is a method for determining the quality of a production vaccine or clone sample, which comprises (a) providing a production vaccine or clone sample nucleic acid; (b) preparing a mixture of the sample nucleic acid with a solid support described herein having solid phase nucleic acid under conditions in which a single molecule of the sample nucleic acid hybridizes to a solid support molecule; (c) contacting the mixture with extension agents under conditions in which solid phase nucleic acid hybridized to sample nucleic acid is extended; (d) amplifying extended nucleic acid; (e) analyzing the sequence of amplified nucleic acid of part (d); and (f) comparing a sequence determined by part (e) to a clone or vaccine reference sequence, whereby the quality of the production clone or vaccine is determined based upon the comparison in part (f). The comparison in part (f) may be the degree of identity between the entire sequence or subsequence of the production clone or vaccine to a corresponding sequence in the reference clone or vaccine. A reference sequence may be obtained from a different production lot or a progenitor clone or vaccine, for example. In some embodiments the sample may be processed before step (b), by purifying the nucleic acid in the sample and/or fragmenting the sample nucleic acid, for example. Part (d) is optional in certain embodiments: the extended solid phase nucleic acid of (c) may be analyzed by sequencing (e), without amplification (d), using sequencing by synthesis methods described above.

EXAMPLES

The following example illustrates certain embodiments and does not limit the invention.

Example 1: Sequence Analysis Methodology

Described hereafter is methodology for performing nucleic acid sequence analyses described herein. Synthesized oligonucleotides containing probe, primer and identification sequences are linked to solid support (beads, slides, chips, and the like, and in some embodiments, Dynal® beads) commonly available in the art, via appropriate linkage chemistry. In some embodiments using Dynal® beads, carbxoy-amino linkage chemistry may be used to link synthesized oligonucleotides to the beads. Synthesis of oligonucleotides is well known in the art and a variety of methods to synthesis oligonucleotides and oligonucleotide libraries, including methods which incorporate modified or derivatized nucleotides designed to increase the biological stability of the molecules or to increase the physical stability of the duplex formed between the antisense and sense nucleic acids (e.g., phosphorothioate derivatives and acridine substituted nucleotides) can be chosen. Nucleotide sequences for synthesized oligonucleotides may include any nucleic acid sequence(s) useful for biological or clinical investigation processes (e.g. SNP's, known probe sequences specific to pathogenic microorganisms and the like) including, but not limited to, those applications and uses described herein. In some embodiments synthesized oligonucleotides may be linked to solid support under dilute conditions such that one or only a few oligonucleotides are linked to each individual unit of solid support (1, 2, 3, 4, 5, or up to 10 linked synthesized oligonucleotides), when using beads or particles as solid support, for example. In some embodiments with more than one linked oligonucleotide, the oligonucleotides linked are not identical in sequence.

Sample nucleic acid is prepared and contacted with the synthesized oligonucleotides containing probe, primer and identification sequences linked to solid support (hereinafter referred to as solid phase oligonucleotides, or solid phase oligos). Sample nucleic acid may be prepared by any means commonly known in the art, including but not limited to cell lysis procedures using chemical, physical or electrolytic lysis methods. For example, chemical methods generally employ lysing agents to disrupt the cells and extract the nucleic acids from the cells, followed by treatment with chaotropic salts. Physical methods such as freeze/thaw followed by grinding, the use of cell presses and the like are also useful if intact proteins are desired. High salt lysis procedures are also commonly used. These procedures can be found in Current Protocols in Molecular Biology, John Wiley & Sons, N.Y., 6.3.1-6.3.6 (1989), incorporated herein in its entirety.

Sample nucleic acid may be further manipulated or prepared following cell lysis and nucleic acid isolation. Methods of nucleic acid preparation including but not limited to, shearing, size fractionation, purification, methylation or demethylation, restriction nuclease treatment, addition of nucleotides or linkers (defined herein as short oligomers of nucleotides of specific or non-specific sequence), incorporation of detectable label and the like, may be used to prepare sample nucleic acids for contact with solid phase oligonucleotides. For example, genomic sample DNA may be sheared, diluted and mixed with a molar excess of beads, in some embodiments. Genomic DNA mixed, under dilute conditions, with a molar excess of solid phase oligos (using molar ratios described above), enables binding of one sample nucleic acid molecule to one bead, in some embodiments. Sample nucleic acid and solid phase oligos can be hybridized under any conditions useful for hybridization known in the art, non-limiting examples of which are described above. Following hybridization, the solid phase oligo/sample nucleic acid complex may be isolated, in some embodiments. Isolation of these complexes may allow removal of possible amplification step contaminants.

The beads and sample DNA may be mixed with polymerase chain reaction components and the mixture may be emulsified with mineral oil (e.g., Margulies et al., "Genome sequencing in open microfabricated high density picoliter reactors," Nature: 376-380 (2005); Kojima et al., "PCR amplification from single DNA molecules on magnetic beads in emulsion: application for high-throughput screening of transcription factor targets," Nucleic Acids Research 33(17) (2005)), under conditions, that allow extension and amplification (linear or exponential, as required by the artisan) of the solid phase oligonucleotide using hybridized sample nucleic acid as the template. The extension of solid phase oligos, using sample nucleic acid as a template, results in an extended solid phase nucleic acid that is substantially complimentary (i.e., antisense) to the sample nucleic acid.

After solid phase nucleic acids are extended, the extended nucleic acids may be sequenced by any sequencing protocol known in the art including, but not limited to, sequencing methodologies described above (e.g., sequencing by ligation, pyrosequencing, sequencing by synthesis) or as described in, Bently, "Whole genome resequencing," Curr Opin Genet Dev 16(6):545-52 (2006); Shendure et al., "Accurate multiplex polony sequencing of an evolved bacterial genome," Science 309(5741):1728-32 (2005); Ju et al., "Four-color DNA sequencing by synthesis using cleavable fluorescent nucleotide reversible terminators," Proc Natl Acad Sci USA 103(52):19635-40 (2006)), for example. Raw sequence data may be stored for later sequence assembly and analysis.

Sequence reads may be assembled using assembly algorithms into full-length sequences (e.g., Warren et al. "Assembling millions of short DNA sequences using SSAKE," Bioinformatics 23(4):500-1 (2006); Jeck et al., "Extending assembly of short DNA sequences to handle error," Bioinformatics 23(21):2942-4 (2007)). After analyzing sequence data, specific determinations may be made according to the method, process, or application performed by the artisan (e.g., detection of the presence or absence of pathogenic organisms, quality control for bio-reactor processes, allelic frequency determinations, detection of allelic variations in gene expression and the like).

The example described above may be used to detect, identify, and sequence viral nucleic acids found in viral mixtures (e.g., finding hepatitis B genotypes or serotypes in a hepatitis viral mixture), or mixed viral populations as might be found in samples isolated from environmental sources or from immuno-deficient organisms. The methodology for detecting, identifying, and sequencing viral nucleic acids is substantially similar to that described above for nucleic acid sequencing.

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents.

Modifications may be made to the foregoing without departing from the basic aspects of the invention. Although the invention has been described in substantial detail with reference to one or more specific embodiments, those of ordinary skill in the art will recognize that changes may be made to the embodiments specifically disclosed in this application, yet these modifications and improvements are within the scope and spirit of the invention.

The invention illustratively described herein suitably may be practiced in the absence of any element(s) not specifically disclosed herein. Thus, for example, in each instance herein any of the terms "comprising," "consisting essentially of," and "consisting of" may be replaced with either of the other two terms. The terms and expressions which have been employed are used as terms of description and not of limitation, and use of such terms and expressions do not exclude any equivalents of the features shown and described or portions thereof, and various modifications are possible within the scope of the invention claimed. The term "a" or "an" can refer to one of or a plurality of the elements it modifies (e.g., "a reagent" can mean one or more reagents) unless it is contextually clear either one of the elements or more than one of the elements is described. The term "about" as used herein refers to a value within 10% of the underlying parameter (i.e., plus or minus 10%), and use of the term "about" at the beginning of a string of values modifies each of the values (i.e., "about 1, 2 and 3" is about 1, about 2 and about 3). For example, a weight of "about 100 grams" can include weights between 90 grams and 110 grams. Thus, it should be understood that although the present invention has been specifically disclosed by representative embodiments and optional features, modification and variation of the concepts herein disclosed may be resorted to by those skilled in the art, and such modifications and variations are considered within the scope of this invention.

Embodiments of the invention are set forth in the claim(s) that follow(s).

What is claimed is:

1. A method for analyzing a sample nucleic acid sequence, which comprises:
   a. preparing a mixture comprising the sample nucleic acid and a collection of solid supports under conditions in which a single molecule of the sample nucleic acid hybridizes to a nucleic acid molecule on a solid support in the collection, wherein:
      (i) the nucleic acid molecules on each solid support in the collection comprise a single-stranded solid phase nucleic acid species including a primer sequence, an identifier sequence and a probe sequence;
      (ii) at least one nucleic acid molecule of the solid phase nucleic acid species on each of the solid supports in the collection has a unique probe sequence different than a probe sequence of the solid phase nucleic acid species of the other solid supports in the collection;
      (iii) the probe sequence of each solid phase nucleic acid species on a solid support in the collection hybridizes to a subsequence of the sample nucleic acid sequence when the probe sequence is complementary to a nucleotide subsequence in the sample nucleic acid sequence;
      (iv) the solid phase nucleic acid species on each solid support in the collection share a unique identifier sequence with the other solid phase nucleic acid species on the solid support, wherein the unique identifier sequence is different than the identifier sequences of the solid phase nucleic acid species of the other solid supports in the collection;
   b. contacting the mixture with extension reagents under conditions in which solid phase nucleic acid species hybridized to the sample nucleic acid in (iii) are extended by the reagents, whereby extended solid phase nucleic acid species comprising the unique identifier sequence of the solid support in (iii) and subsequences of the sample nucleic acid are obtained;
   c. amplifying the extended solid phase nucleic acid species of (b) by linear amplification; and
   d. determining the sequences of the amplification products of (c); whereby the sample nucleic acid sequence is analyzed.

2. The method of claim 1, wherein the solid phase nucleic acid species of one or more solid supports in the collection do not share a common probe sequence.

3. The method of claim 1, wherein the solid phase nucleic acid species of one or more solid supports in the collection share a common probe sequence.

4. The method of claim 1, wherein the solid support is a bead or particle.

5. The method of claim 4, wherein the bead or particle is a microbead, a nanobead, a microparticle or a nanoparticle.

6. The method of claim 4, wherein the bead or particle comprises a gel.

7. The method of claim 4, wherein the bead or particle comprises a magnetic material.

8. The method of claim 1, wherein determining the sequences of the amplification products in (d) comprises: hybridizing the amplification products to an oligonucleotide comprising a sequence complementary to an immobilized capture nucleic acid sequence, thereby immobilizing the amplification products; and sequencing the immobilized amplification products.

9. The method of claim 1, wherein the solid phase nucleic acid species of each solid support in the collection share a common primer sequence.

10. The method of claim 1, wherein the primer sequence is a universal primer sequence.

11. The method of claim 1, wherein the solid phase nucleic acid species of all the solid supports in the collection share a common primer sequence.

12. The method of claim 1, wherein the sample nucleic acid comprises DNA.

13. The method of claim 1, wherein the sample nucleic acid comprises fragmented DNA.

14. The method of claim 1, wherein the sample nucleic acid is from a single sample.

15. The method of claim 1, wherein the sample nucleic acid is from a mixture or pool of samples.

16. The method of claim 1, wherein the sample nucleic acid is single-stranded nucleic acid.

17. A method for preparing sample nucleic acid complements, which comprises:
   a. preparing a mixture comprising the sample nucleic acid and a collection of solid supports under conditions in which a single molecule of the sample nucleic acid hybridizes to a nucleic acid molecule on a solid support in the collection, wherein:
      (i) the nucleic acid molecules on each solid support in the collection comprising a single-stranded solid phase nucleic acid species including a primer sequence, an identifier sequence and a probe sequence;
      (ii) at least one nucleic acid molecule of the solid phase nucleic acid species on each of the solid supports in the collection has a unique probe sequence different than a probe sequence of the solid phase nucleic acid species of the other solid supports in the collection;
      (iii) the probe sequence of each solid phase nucleic acid species on a solid support in the collection hybridizes to a subsequence of the sample nucleic acid sequence when the probe sequence is complementary to a nucleotide subsequence in the sample nucleic acid sequence;
      (iv) the solid phase nucleic acid species on each solid support in the collection share a unique identifier sequence with the other solid phase nucleic acid species on the solid support, wherein the unique identifier sequence is different than the identifier sequences of the solid phase nucleic acid species of the other solid supports in the collection; and
   b. contacting the mixture with extension reagents under conditions in which solid phase nucleic acid species hybridized to the sample nucleic acid in (iii) are extended by the reagents, whereby sample nucleic acid complements comprising the shared, unique identifier sequence of the solid support in (iii) and subsequences of the sample nucleic acid are prepared
   c. amplifying the extended solid phase nucleic acid species of (b) by linear amplification.

* * * * *